United States Patent
Arensdorf et al.

(10) Patent No.: US 11,274,335 B2
(45) Date of Patent: Mar. 15, 2022

(54) METHODS FOR THE EPIGENETIC ANALYSIS OF DNA, PARTICULARLY CELL-FREE DNA

(71) Applicant: Bluestar Genomics, Inc., San Francisco, CA (US)

(72) Inventors: Patrick A. Arensdorf, Palo Alto, CA (US); Damek Spacek, Palo Alto, CA (US)

(73) Assignee: BLUESTAR GENOMICS, INC., San Diego, CA (US)

( * ) Notice: Subject to any disclaimer, the term of this patent is extended or adjusted under 35 U.S.C. 154(b) by 0 days.

(21) Appl. No.: 17/118,234

(22) Filed: Dec. 10, 2020

(65) Prior Publication Data

US 2021/0262009 A1 Aug. 26, 2021

Related U.S. Application Data

(63) Continuation of application No. 16/275,237, filed on Feb. 13, 2019.

(60) Provisional application No. 62/630,798, filed on Feb. 14, 2018.

(51) Int. Cl.
| | |
|---|---|
| *C12Q 1/6806* | (2018.01) |
| *C07H 19/06* | (2006.01) |
| *C07H 21/04* | (2006.01) |
| *C07J 1/00* | (2006.01) |
| *C12Q 1/6827* | (2018.01) |

(52) U.S. Cl.
CPC ............ *C12Q 1/6806* (2013.01); *C07H 19/06* (2013.01); *C07H 21/04* (2013.01); *C07J 1/00* (2013.01); *C12Q 1/6827* (2013.01); *C12Q 2523/10* (2013.01); *C12Q 2523/115* (2013.01); *C12Q 2537/164* (2013.01)

(58) Field of Classification Search
None
See application file for complete search history.

(56) References Cited

U.S. PATENT DOCUMENTS

| | | | |
|---|---|---|---|
| 7,582,420 | B2 | 9/2009 | Oliphant et al. |
| 8,106,200 | B2 * | 1/2012 | Burkhardt ................ C01B 6/13 546/13 |
| 8,741,567 | B2 | 6/2014 | He et al. |
| 9,267,117 | B2 | 2/2016 | Guan et al. |
| 2017/0253924 | A1 | 9/2017 | Lu et al. |
| 2020/0370114 | A1 | 11/2020 | Song et al. |

FOREIGN PATENT DOCUMENTS

| | | |
|---|---|---|
| WO | 2014074450 A1 | 5/2014 |
| WO | 2015021282 A1 | 2/2015 |
| WO | 2017176630 A1 | 10/2017 |
| WO | 2019136413 A1 | 7/2019 |
| WO | WO-2019136413 A1 * | 7/2019 ........... C12Q 1/6827 |

OTHER PUBLICATIONS

Booth et al., "Quantitative sequencing of 5-Methylcytosine and 5-Hydroxymethylcytosine at Single-Base Resolution", (2012) Science 336: 934-937 (Year: 2012).*
"PCT Search Report and Written Opinion, PCT/US2019/017902", dated Apr. 11, 2019.
Liu, Yibin, et al., "Bisulfite-free direct detection of 5-methylcytosine and 5-hydroxymethylcytosine at base resolution", Mature Biotechnology 37, Feb. 25, 2019, pp. 424-429.
Mestor, Colm E., et al., "Tissue type is a major modifier of the 5-hydroxymethylcytosine content of human genes", Gnome Research, vol. 22; Cold Spring Harbor Laboratory Press, Sep. 6, 2016, pp. 467-477.
Robertson, Adam B., et al., "A novel method for the efficient and selective identification of 5-hydroxymethylcytosine in genomic DNA", Nucleic Acids Research, vol. 39, No. 8, Feb. 7, 2011, pp. 1-10.
Ruhaak, L. Renee, et al., "2-Picoline-borane: A non-toxic reducing agent for oligosaccharida labeling by reductive amination", Proteomics, vol. 10, Mar. 24, 2010, pp. 2330-2336.
Song, Chunxiao, et al., U.S. Appl. No. 62/614,798, filed Jan. 8, 2018.
Song, Chunxiao, et al., U.S. Appl. No. 62/660,523, filed Apr. 20, 2018.
Song, Chunxiao, et al., U.S. Appl. No. 62/771,409, filed Nov. 26, 2018.
Song, Chunxiao, "Bisulfite-free, base resolution, and quantitative identification of cytosine modifications", Keystone Symposia Conference, DNA & RNA Methylation, Ludwig Institute for Cancer Research, University of Oxford, Jan. 24, 2018, pp. 1-23.
Tahiliani, Mamta, et al., "Conversion of 5-Methylcytosine to 5-Hydroxymethylcytosine in Mammalian DNA by MML Partner TET1", Science vol. 324, 930, May 15, 2009, pp. 930-935.
Yu, Miao, et al., "Tet-assisted bisulfite sequencing of 5-hydroxymethylcytosine", Nature Protocols, vol. 7, No. 12, Nov. 29, 2012, pp. 2159-2170.

(Continued)

*Primary Examiner* — Jehanne S Sitton
*Assistant Examiner* — Daniel W Nielsen
(74) *Attorney, Agent, or Firm* — Dianne E. Reed; VLP Law Group, LLP

(57) ABSTRACT

Methods are provided for the epigenetic analysis of cell-free DNA using organic boranes to convert oxidized 5-methylcytosine residues in the cell-free DNA to dihydrouracil (DHU) residues. Cell-free DNA is contacted with an organic borane selected to successively bring about reduction, deamination, and decarboxylation of oxidized 5-methylcytosine residues such as 5-carboxylcytosine and 5-formylcytosine, resulting in DHU residues in place thereof. Following amplification, the treated cell-free DNA is sequenced, with the DHU residues read as thymine residues. Reaction mixtures, kits and additional methods are also provided, as are related methods for the epigenetic analysis of DNA, including cell-free DNA.

11 Claims, 26 Drawing Sheets

Specification includes a Sequence Listing.

(56) References Cited

OTHER PUBLICATIONS

Ambrogelly, Alexandre, et al., "Screening of Reducing Agents for the PEGylation of Recombinant Human IL-10", Protein J 32, 2013, pp. 337-342.

Song, Chun-Xiao, et al., "Selective chemical labeling reveals the genome-wide distribution of 5-hydroxymethylcytosine", Nat Biotechnol. 29(1), Jan. 2011, pp. 68-72.

* cited by examiner

FIG. 16

SEQUENCE LISTING

```
<160> NUMBER OF SEQ ID NOS: 2

<210> SEQ ID NO 1
<211> LENGTH: 11
<212> TYPE: DNA
<213> ORGANISM: Artificial
<220> FEATURE:
<223> OTHER INFORMATION: Cytosine substitued at 5' position
<220> FEATURE:
<221> NAME/KEY: modified_base
<222> LOCATION: (5)..(7)

<400> SEQUENCE: 1
tcgaccggat c                                                          11

<210> SEQ ID NO 2
<211> LENGTH: 13
<212> TYPE: DNA
<213> ORGANISM: Artificial
```

```
<220> FEATURE:
<223> OTHER INFORMATION: Cytosine substituted at 5' position
<220> FEATURE:
<221> NAME/KEY: modified_base
<222> LOCATION: (12)..(13)

<400> SEQUENCE: 2
gtcgaccgga tcc                                                          13
```

METHODS FOR THE EPIGENETIC ANALYSIS OF DNA, PARTICULARLY CELL-FREE DNA

CROSS-REFERENCE TO RELATED APPLICATIONS

This application is a continuation of U.S. application Ser. No. 16/275,237, filed Feb. 13, 2019, which claims priority under 35 U.S.C. § 119(e)(1) to provisional U.S. application Ser. No. 62/630,798, filed Feb. 14, 2018. The disclosures of the aforementioned applications are incorporated herein by reference in its entirety.

REFERENCE TO SEQUENCE LISTING, TABLES OR COMPUTER PROGRAM LISTING

Reference to Sequence Listing, a table or a computer program listing appendix complies with 37 CFR § 1.821 through 37 CFR § 1.825 and may be in paper or electronic form. The ASCII text file is named 20210510_3599-0001CON_TPO_Sequence_Listing.txt, created on May 5, 2021, and is 1 KB.

TECHNICAL FIELD

The present invention relates generally to biotechnology, and more particularly relates to the epigenetic analysis of cell-free DNA. The invention finds utility in the fields of genomics, medicine, diagnostics, and epigenetic research.

BACKGROUND

The field of epigenetics requires the detection of certain DNA modifications, particularly the modified cytosine residues 5-methylcytosine (5mC) and its primary oxidation product 5-hydroxymethylcytosine (5hmC):

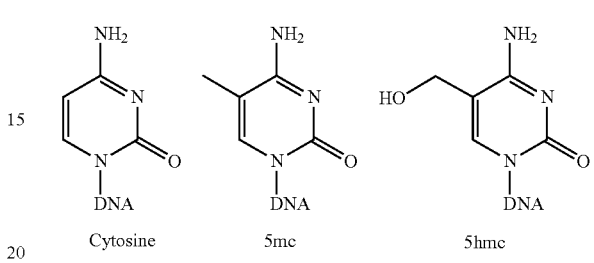

Initially, researchers focused on 5mC, as 5hmC was not identified as a potentially important modification until later. In order to distinguish between unmodified cytosine residues and 5mC residues at single-base resolution, DNA epigenetic analysis has typically required the use of a bisulfite reagent, insofar as bisulfite rapidly converts cytosine residues to dihydrouracil residues via the process of Scheme 1

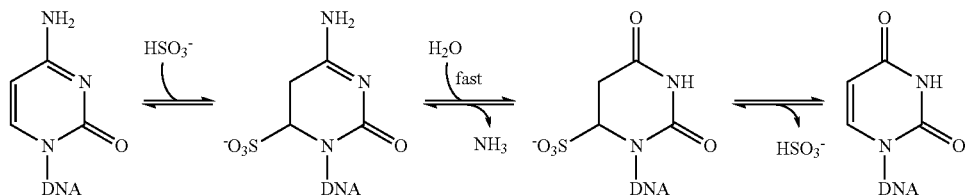

while exhibiting a very low conversion rate with 5mC, as shown in Scheme 2.

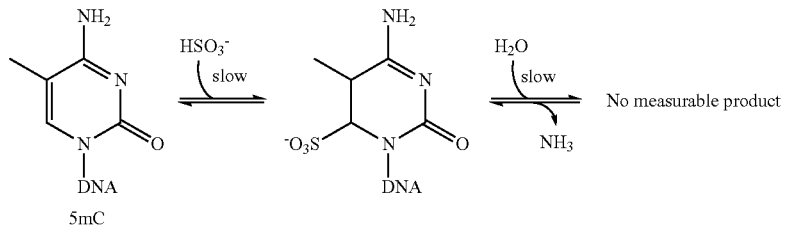

There are two serious drawbacks to the use of bisulfite in single-base resolution sequencing, however. First, bisulfite results in significant degradation of the DNA, as high as 90% or more. This precludes implementation of the technique with very small amounts of DNA, such as in the cell-free DNA context, as cell-free DNA typically contains only a few nanograms DNA per mL of plasma. Second, the bisulfite method presumes the complete conversion of cytosine to thymine, rendering the bisulfite process susceptible to false positives, with even a 1% non-conversion rate leading to false positive readings of 10-15% or more. The reliance on complete conversion also results in primer design difficulty, a low mapping rate of sequencing reads, and an overall increase in sequencing cost.

As the field of epigenetics has evolved, the detection of another DNA modification, 5hmC, proved to be potentially as important as the detection of 5mC. While the 5mC modification generally occurs within CpG dinucleotides, native 5hmC residues tend to appear in other locations. In addition, the occurrence of 5hMC is much less frequent than that of 5mC, at a ratio typically approximating 10:1, depending on tissue type (see Nestor et al. (2012) Genome Biology 13:R84), with 5mC representing about 1% of all DNA bases. The molecular function of 5hmC is just beginning to be understood, although it has been established that 5hmC is involved in a variety of processes, including transcription, DNA demethylation, and, in the case of aberrant 5hmC patterns, in tumorigenesis. See Tahiliani et al. (2009) Science 324(5929):930-035 (2009); Guo et al. (2011) Cell 145:423-434; Wu et al. (2011) Genes & Development 25:679-684; Ko et al. (2010) Nature 468:839-843; and Robertson et al. (2011) Biochem. Biophys. Res. Comm. 411(1):40-3. It is also known that 5hmC is a stable DNA modification, formed from the catalytic oxidation of 5mC by a Ten-Eleven Translocation (TET) enzyme such as TET1.

Bisulfite sequencing does not distinguish between 5mC and 5hmC, and, therefore, other methods for individually detecting 5mC and 5hmC residues are necessary. As noted above, 5hmC appears far less often than 5mC, so that any method for detecting 5hmC needs to exhibit high efficiency, with respect to the fraction of all 5hmC residues that are identified, as well as high selectivity, meaning that substantially all residues identified as 5hmC should, in fact, be 5hmC residues. Several methods have been reported for detecting 5hmC in DNA that involve glucosylation with a T4 bacteriophage enzyme, β-glucosyltransferase (β-GT), as the enzyme selectively glucosylates 5hmC without modifying 5mC, as illustrated in Scheme 3:

Scheme 3

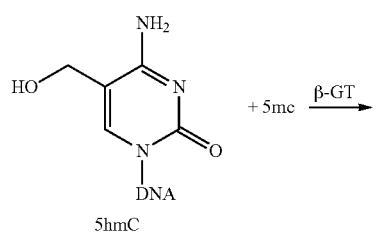

5hmC

-continued

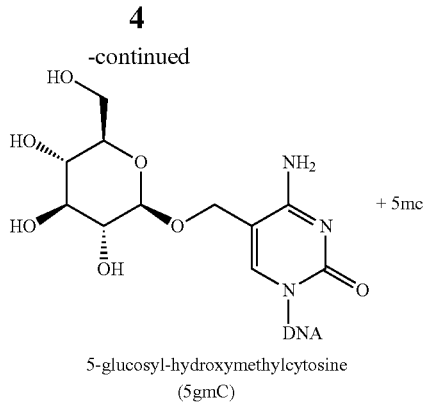

5-glucosyl-hydroxymethylcytosine
(5gmC)

For example, Robertson et al. describe the use of a J-binding protein to pull down target DNA fragments with glucosylated 5hmC residues (see Robertson et al. (2011) Nuc. Acids Res. 39, e55). Others have proposed the possibility of using antibodies raised against 5hmC to distinguish between 5mC and 5hmC. Most recently, selective glucosylation of 5hmC residues has been carried out in a manner that provides an azide group at those locations, by, for example, glucosylating with uridine diphospho (UDP) glucose functionalized at the 6-position with an azide moiety. This selective reaction of 5hmC residues to provide azide groups at those locations is followed by a spontaneous 1,3-cycloaddition reaction with alkyne-functionalized biotin, a type of reaction commonly termed "click chemistry" in the field. The DNA fragments containing these biotinylated 5hmC residues can then be pulled down with streptavidin beads. See International Patent Publication No. WO 2017/176630 to Quake et al., which describes such a method in detail. Also see U.S. Pat. No. 8,741,567 to He et al. and U.S. Patent Publication No. US 2017/0253924 to Lu et al., pertaining to a method for distinguishing between 5mC and 5hmC by selectively glucosylating of 5hmC residues.

There remains a need for alternative methods of carrying out single-base resolution sequencing, however, particularly with extremely small sample sizes, e.g., those used in cell-free DNA analysis. An ideal method would detect modified cytosine residues at single-base resolution, without affecting normal cytosine residues. Optimally, the method can be readily adapted to detect 5hmC in addition to or instead of 5mC, even with single DNA strands containing both 5mC and 5hmC residues. A method for separately detecting 5hmC as well as 5mC at base resolution would potentially be of enormous importance, as the process would enable mapping of both epigenetic markers. Use of non-toxic reagents and mild reaction conditions would be preferred, so as to avoid or at least minimize DNA degradation. Finally, an ideal method would enable tagging DNA fragments with at least one molecular barcode (or "sequence barcode"), a short, unique oligonucleotide sequence that, during sequencing, serves to identify one or more features of each DNA strand or fragment that contains it.

SUMMARY OF THE INVENTION

Accordingly, the present invention addresses the above needs in the art by providing a novel method for the epigenetic analysis of cell-free DNA.

In a first embodiment, a method is provided for converting oxidized 5-methylcytosine residues in cell-free DNA to dihydrouracil residues, where the method comprises contacting cell-free DNA containing at least one oxidized 5-methylcytosine residue selected from 5-carboxylcytosine, 5-formylcytosine, and combinations thereof, with an organic borane effective to reduce, deaminate, and either decarboxylate or deformylate the at least one oxidized 5-methylcytosine residue, thereby providing a dihydrouracil residue in place thereof.

In one aspect of the aforementioned embodiment, the organic borane comprises a complex of borane and a nitrogen-containing compound selected from nitrogen heterocycles and tertiary amines.

In another aspect of the embodiment, reduction, deamination, and decarboxylation are carried out without isolation of any intermediate, i.e., as a "one-pot" or "one-tube" reaction.

In another aspect of the embodiment, the method is carried out in the absence of any bisulfite reagents.

In still another aspect of the embodiment, the cell-free DNA comprises selected regions of cell-free DNA, where "regions" refer to either location along a DNA strand or a sequence-based composition. In a related aspect, the cell-free DNA comprises selected fragments of cell-free DNA, in addition to or instead of selected regions of cell-free DNA.

In a further aspect of the embodiment, the cell-free DNA comprises double-stranded DNA.

In an additional aspect of the embodiment, the cell-free DNA comprises single-stranded DNA.

In another embodiment, a reaction mixture is provided that comprises:

(a) a sample of cell-free DNA containing at least one oxidized 5-methylcytosine residue selected from 5-carboxylcytosine, 5-formylcytosine, and combinations thereof; and (b) an organic borane effective to effective to reduce, deaminate, and either decarboxylate or deformylate the at least one oxidized 5-methylcytosine residue.

In an additional embodiment, a method is provided for detecting the presence and location of 5-methylcytosine residues in cell-free DNA, wherein the method comprises:

(a) modifying 5-hydroxymethylcytosine residues in fragmented, adapter-ligated cell-free DNA to provide an affinity tag thereon, wherein the affinity tag enables removal of modified 5-hydroxymethylcytosine-containing DNA from the cell-free DNA;

(b) removing the modified 5-hydroxymethylcytosine-containing DNA from the cell-free DNA, leaving DNA containing unmodified 5-methylcytosine residues;

(c) oxidizing the unmodified 5-methylcytosine residues to give DNA containing oxidized 5-methylcytosine residues selected from 5-carboxylcytosine, 5-formylcytosine, and combinations thereof;

(d) contacting the DNA containing oxidized 5-methylcytosine residues with an organic borane effective to reduce, deaminate, and either decarboxylate or deformylate the oxidized 5-methylcytosine residues, thereby providing DNA containing dihydrouracil residues in place of the oxidized 5-methylcytosine residues;

(e) amplifying and sequencing the DNA containing dihydrouracil residues;

(f) determining a 5-methylation pattern from the sequencing results in (e).

In one aspect of this embodiment, the method further includes:

(g) identifying a hydroxymethylation pattern in the 5-hydroxymethylcytosine-containing DNA removed from the cell-free DNA sample in step (b).

In another aspect of the embodiment, the affinity tag is comprised of biotin, and step (a) comprises selective labeling of 5-hydroxymethylcytosine residues with biotin. In a related aspect, step (b) comprises contacting the biotinylated DNA with support-bound streptavidin.

In another aspect of the embodiment, the affinity tag is comprised of a selected oligonucleotide having a predetermined sequence, and step (a) comprises selective labeling of 5-hydroxymethylcytosine residues with the oligonucleotide. In a related aspect, step (b) comprises contacting the oligonucleotide-labeled DNA with a support-bound oligonucleotide comprising a sequence substantially complementary to the predetermined sequence.

In an additional aspect of the embodiment, step (c) is carried out enzymatically, e.g., using a Ten-Eleven Translocation (TET) enzyme.

In a further aspect of the embodiment, the cell-free DNA sample comprises at least one DNA strand having at least one 5-methylcytosine residue and at least one 5-hydroxymethylcytosine residue.

In an additional aspect, the method further comprises, prior to step (e), attaching at least one sequence barcode to each of a plurality of double-stranded DNA fragments. In a related aspect, the at least one sequence barcode comprises an individual barcode designating a feature of the DNA fragment corresponding to a process undergone by the DNA fragment.

In another embodiment, the invention provides a kit for converting 5-methylcytosine residues and 5-hydroxymethylcytosine residues in cell-free DNA to dihydrouracil residues, comprising a reagent for oxidizing the 5-methylcytosine and 5-hydroxymethylcytosine residues to provide oxidized 5-methylcytosine residues, and an organic borane effective to reduce, deaminate, and either decarboxylate or deformylate the oxidized 5-methylcytosine residues.

In a further embodiment, the invention provides a kit for identifying 5-methylcytosine residues in a cell-free DNA sample, comprising individual reagent compositions for: modifying 5-hydroxymethylcytosine residues to provide a affinity tag thereon; removing the modified 5-hydroxymethylcytosine residues from the sample; oxidizing unmodified 5-methylcytosine residues to provide oxidized 5-methylcytosine residues; and an organic borane effective to reduce, deaminate, and either decarboxylate or deformylate the oxidized 5-methylcytosine residues.

BRIEF DESCRIPTION OF THE DRAWINGS

FIGS. 7(a) and (b), Sequence ID NO. 2).

FIG. 16 schematically illustrates the "biotin/native 5mC" enrichment method of the invention.

DETAILED DESCRIPTION OF THE INVENTION

1. Definitions and Terminology

Figure 1:
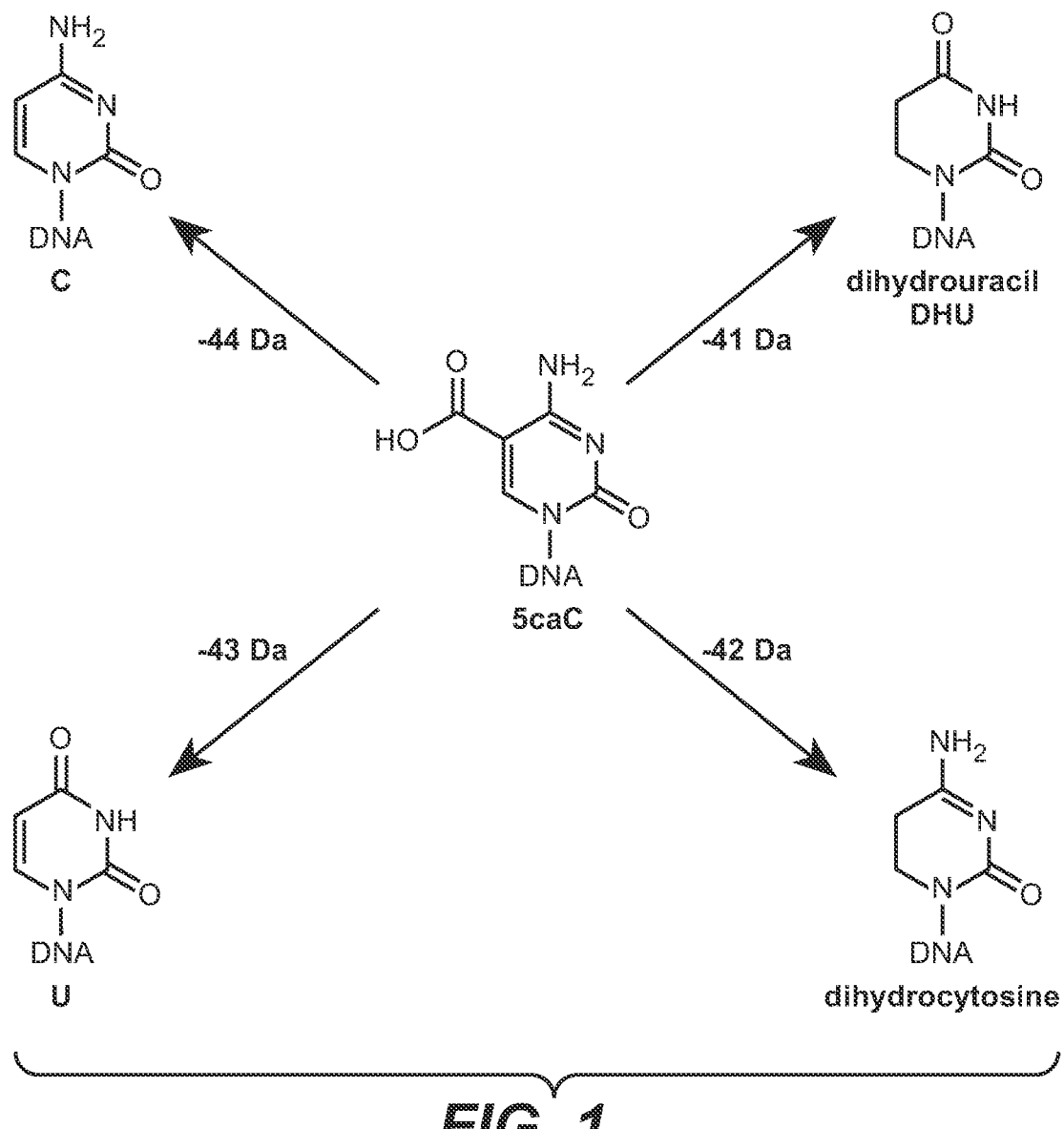
FIG. 1 schematically illustrates the hypothetical reaction products of 2-picoline borane with 5-carboxylcytosine.

Unless defined otherwise, all technical and scientific terms used herein have the meaning commonly understood by one of ordinary skill in the art to which the invention pertains. Specific terminology of particular importance to the description of the present invention is defined below. Other relevant terminology is defined in International Patent Publication No. WO 2017/176630 to Quake et al. for "Noninvasive Diagnostics by Sequencing 5-Hydroxymethylated Cell-Free DNA." The aforementioned patent publication as well as all other patent documents and publications referred to herein are expressly incorporated by reference.

In this specification and the appended claims, the singular forms "a," "an" and "the" include plural referents unless the context clearly dictates otherwise. Thus, for example, "a component" refers not only to a single component but also to a combination of two or more different components, and the like.

Numeric ranges are inclusive of the numbers defining the range. Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention. Accordingly, the terms defined immediately below are more fully defined by reference to the specification as a whole.

Unless defined otherwise, all technical and scientific terms used herein have the same meaning as commonly understood by one of ordinary skill in the art to which this invention belongs. Singleton, et al., Dictionary of Microbiology and Molecular Biology, 2d Ed. (New York: John Wiley and Sons, 1994), and Hale & Markham, The Harper Collins Dictionary of Biology (New York: Harper Perennial, 1991) provide one of ordinary skill in the art with the general meaning of many of the terms used herein. Still, certain terms are defined below for the sake of clarity and ease of reference.

The term "sample" as used herein relates to a material or mixture of materials, typically, although not necessarily, in liquid form, containing one or more analytes of interest.

The term "nucleic acid sample," as used herein denotes a sample containing at least one nucleic acid. Nucleic acid samples used herein may be complex in that they may contain multiple different molecules that contain nucleic acid sequences. Genomic DNA from a mammal (e.g., mouse or human) are types of complex samples. Complex samples may have at least 10,000, at least 100,000, at least $10^6$, at least $10^7$, at least $10^8$ or at least $10^9$ or more different nucleic acid molecules. A DNA target may originate from any source such as genomic DNA, or an artificial DNA construct. Any sample containing nucleic acid, e.g., genomic DNA made from tissue culture cells or a sample of tissue, may be employed herein. A nucleic acid sample can be made from any suitable source, including a sample of tooth, bone, hair or bone, etc.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 to Honkanen et al. and the references cited therein) which can hybridize with naturally occurring nucleic acids in a sequence specific manner analogous to that of two naturally occurring nucleic acids, e.g., can participate in Watson-Crick base pairing interactions. Naturally occurring nucleotides include guanine, cytosine, adenine and thymine (G, C, A and T, respectively). DNA and RNA have a deoxyribose and ribose sugar backbone, respectively, whereas PNA's backbone is composed of repeating N-(2-aminoethyl)-glycine units linked by peptide bonds. In PNA various purine and pyrimidine bases are linked to the backbone by methylene carbonyl bonds. A locked nucleic acid (LNA), often referred to as inaccessible RNA, is a modified RNA nucleotide. The ribose moiety of an LNA nucleotide is modified with an extra bridge connecting the 2' oxygen and 4' carbon. The bridge "locks" the ribose in the 3'-endo (North) conformation, which is often found in the A-form duplexes. LNA nucleotides can be mixed with DNA or RNA residues in the oligonucleotide whenever desired. The term "unstructured nucleic acid," or "UNA," is a nucleic acid containing non-natural nucleotides that bind to each other with reduced stability.

For example, an unstructured nucleic acid may contain a G' residue and a C' residue, where these residues correspond to non-naturally occurring forms, i.e., analogs of G and C that base pair with each other with reduced stability, but retain an ability to base pair with naturally occurring C and G residues, respectively. Unstructured nucleic acid is described U.S. Patent Publication No. US 2005/0233340 to Barrett et al., which is incorporated by reference herein for disclosure of UNA. Also included in this definition are ZNAs, i.e., zip nucleic acids.

The term "oligonucleotide" as used herein denotes a single-stranded multimer of nucleotide of from about 2 to 200 nucleotides, up to 500 nucleotides in length. Oligonucleotides may be synthetic or may be made enzymatically, and, in some embodiments, are 30 to 150 nucleotides in length. Oligonucleotides may contain ribonucleotide monomers (i.e., may be oligoribonucleotides) and/or deoxyribonucleotide monomers. An oligonucleotide may be 10 to 20, 21 to 30, 31 to 40, 41 to 50, 51 to 60, 61 to 70, 71 to 80, 80 to 100, 100 to 150 or 150 to 200 nucleotides in length, for example.

The term "hybridization" refers to the process by which a strand of nucleic acid joins with a complementary strand through base pairing as known in the art. A nucleic acid is considered to be "selectively hybridizable" to a reference nucleic acid sequence if the two sequences specifically hybridize to one another under moderate to high stringency hybridization and wash conditions. Moderate and high stringency hybridization conditions are known (see, e.g., Ausubel, et al., Short Protocols in Molecular Biology, 3rd ed., Wiley & Sons 1995 and Sambrook et al., Molecular Cloning: A Laboratory Manual, Third Edition, 2001 Cold Spring Harbor, N.Y.). One example of high stringency conditions includes hybridization at about 42° C. in 50% formamide, 5×SSC, 5×Denhardt's solution, 0.5% SDS and 100 µg/ml denatured carrier DNA followed by washing two times in 2×SSC and 0.5% SDS at room temperature and two additional times in 0.1×SSC and 0.5% SDS at 42° C.

The term "primer" refers to an oligonucleotide, either natural or synthetic, which, upon forming a duplex with a polynucleotide template, is capable of acting as a point of initiation of nucleic acid synthesis and being extended from its 3' end along the template so that an extended duplex is formed. The sequence of nucleotides added during the extension process is determined by the sequence of the template polynucleotide. Usually primers are extended by a DNA polymerase. Primers are generally of a length compatible with their use in synthesis of primer extension products, and are usually in the range of between 8 to 100 nucleotides in length, such as 10 to 75, 15 to 60, 15 to 40, 18 to 30, 20 to 40, 21 to 50, 22 to 45, 25 to 40, and so on. Typical primers can be in the range of between 10-50 nucleotides long, such as 15-45, 18-40, 20-30, 21-25 and so on, and any length between the stated ranges. In some embodiments, the primers are usually not more than about 10, 12, 15, 20, 21, 22, 23, 24, 25, 26, 27, 28, 29, 30, 35, 40, 45, 50, 55, 60, 65, or 70 nucleotides in length.

The terms "duplex" and "duplexed" are used interchangeably herein to describe two complementary polynucleotides that are base-paired, i.e., hybridized together.

The terms "determining," "measuring," "evaluating," "assessing," "assaying," and "analyzing" are used interchangeably herein to refer to any form of measurement, and include determining if an element is present or not. These terms include both quantitative and/or qualitative determinations. Assessing may be relative or absolute. "Assessing the presence of" thus includes determining the amount of a moiety present, as well as determining whether it is present or absent.

The term "using" has its conventional meaning, and, as such, means employing, e.g., putting into service, a method or composition to attain an end. For example, if a program is used to create a file, a program is executed to make a file, the file usually being the output of the program. In another example, if a computer file is used, it is usually accessed, read, and the information stored in the file employed to attain an end. Similarly, if a unique identifier, e.g., a barcode is used, the unique identifier is usually read to identify, for example, an object or file associated with the unique identifier.

The term "ligating," as used herein, refers to the enzymatically catalyzed joining of the terminal nucleotide at the 5' end of a first DNA molecule to the terminal nucleotide at the 3' end of a second DNA molecule; the complementary strands may also be joined; e.g. 3' to 5'; or together as in the case of double-stranded DNA.

A "plurality" contains at least 2 members. In certain cases, a plurality may have at least 10, at least 100, at least 10,000, at least 100,000, at least $10^6$, at least $10^7$, at least $10^8$ or at least $10^9$ or more members.

If two nucleic acids are "complementary," each base of one of the nucleic acids base pairs with corresponding nucleotides in the other nucleic acid. Two nucleic acids do not need to be perfectly complementary in order to hybridize to one another.

The term "separating," as used herein, refers to physical separation of two elements (e.g., by size or affinity, etc.) as well as degradation of one element, leaving the other intact.

The term "sequencing," as used herein, refers to a method by which the identity of at least 10 consecutive nucleotides (e.g., the identity of at least 20, at least 50, at least 100 or at least 200 or more consecutive nucleotides) of a polynucleotide is obtained.

The terms "next-generation sequencing" or "high-throughput sequencing", as used herein, refer to the so-called parallelized sequencing-by-synthesis or sequencing-by-ligation platforms currently employed by Illumina, Life Technologies, and Roche, etc. Next-generation sequencing methods may also include nanopore sequencing methods such as that commercialized by Oxford Nanopore Technologies, electronic detection methods such as Ion Torrent technology commercialized by Life Technologies, and single-molecule fluorescence-based methods such as that commercialized by Pacific Biosciences.

The term "adapter" refers to a nucleic acid that is ligatable to both strands of a double-stranded DNA molecule. In one embodiment, an adapter may be a hairpin adapter (i.e., one molecule that base pairs with itself to form a structure that has a double-stranded stem and a loop, where the 3' and 5' ends of the molecule ligate to the 5' and 3' ends of the double-stranded DNA molecule, respectively). In another embodiment, an adapter may be a Y-adapter. In another embodiment, an adapter may itself be composed of two distinct oligonucleotide molecules that are base paired with one another. As would be apparent, a ligatable end of an adapter may be designed to be compatible with overhangs made by cleavage by a restriction enzyme, or it may have blunt ends or a 5' T overhang. The term "adapter" refers to double-stranded as well as single-stranded molecules. An adapter can be DNA or RNA, or a mixture of the two. An adapter containing RNA may be cleavable by RNase treatment or by alkaline hydrolysis. An adapter may be 15 to 100 bases, e.g., 50 to 70 bases, although adapters outside of this range are envisioned.

The term "adapter-ligated," as used herein, refers to a nucleic acid that has been ligated to an adapter. The adapter can be ligated to a 5' end and/or a 3' end of a nucleic acid molecule. As used herein, the term "adding adapter sequences" refers to the act of adding an adapter sequence to the end of fragments in a sample. This may be done by filling in the ends of the fragments using a polymerase, adding an A tail, and then ligating an adapter comprising a T overhang onto the A-tailed fragments.

The term "asymmetric adapter", as used herein, refers to an adapter that, when ligated to both ends of a double stranded nucleic acid fragment, will lead to a top strand that contains a 5' tag sequence that is not the same as or complementary to the tag sequence at the 3' end. Examples of asymmetric adapters are described in U.S. Pat. Nos. 5,712,126 and 6,372,434 to Weissman et al., and International Patent Publication No. WO 2009/032167 to Bignell et al. An asymmetrically tagged fragment can be amplified by two primers: a first primer that hybridizes to a first tag sequence added to the 3' end of a strand; and a second primer that hybridizes to the complement of a second tag sequence added to the 5' end of a strand. Y-adapters and hairpin adapters (which can be cleaved, after ligation, to produce a "Y-adapter") are examples of asymmetric adapters.

The term "Y-adapter" refers to an adapter that contains: a double-stranded region and a single-stranded region in which the opposing sequences are not complementary. The end of the double-stranded region can be joined to target molecules such as double-stranded fragments of genomic DNA, e.g., by ligation or a transposase-catalyzed reaction. Each strand of an adapter-tagged double-stranded DNA that has been ligated to a Y-adapter is asymmetrically tagged in that it has the sequence of one strand of the Y-adapter at one end and the other strand of the Y-adapter at the other end. Amplification of nucleic acid molecules that have been joined to Y-adapters at both ends results in an asymmetrically tagged nucleic acid, i.e., a nucleic acid that has a 5' end containing one tag sequence and a 3' end that has another tag sequence.

The term "hairpin adapter" refers to an adapter that is in the form of a hairpin. In one embodiment, after ligation the hairpin loop can be cleaved to produce strands that have non-complementary tags on the ends. In some cases, the loop of a hairpin adapter may contain a uracil residue, and the loop can be cleaved using uracil DNA glycosylase and endonuclease VIII, although other methods are known.

The term "adapter-ligated sample", as used herein, refers to a sample that has been ligated to an adapter. As would be understood given the definitions above, a sample that has been ligated to an asymmetric adapter contains strands that have non-complementary sequences at the 5' and 3' ends.

An "oligonucleotide binding site" refers to a site to which an oligonucleotide hybridizes in a target polynucleotide. If an oligonucleotide "provides" a binding site for a primer, then the primer may hybridize to that oligonucleotide or its complement.

The term "strand" as used herein refers to a single strand of a nucleic acid made up of nucleotides covalently linked together by covalent bonds, e.g., phosphodiester bonds. In a cell, DNA usually exists in a double-stranded form, and as such, has two complementary strands of nucleic acid referred to herein as the "top" and "bottom" strands. In certain cases, complementary strands of a chromosomal region may be referred to as "plus" and "minus" strands, "positive" and "negative" strands, the "first" and "second" strands, the "coding" and "noncoding" strands, the "Watson" and "Crick" strands or the "sense" and "antisense" strands. The assignment of a strand as being a top or bottom strand is arbitrary and does not imply any particular orientation, function or structure. The nucleotide sequences of the first strand of several exemplary mammalian chromosomal regions (e.g., BACs, assemblies, chromosomes, etc.) is known, and may be found in NCBI's Genbank database, for example.

The term "amplifying" as used herein refers to generating one or more copies of a target nucleic acid, using the target nucleic acid as a template.

The terms "enrich" and "enrichment" refer to a partial purification of analytes that have a certain feature (e.g., nucleic acids that contain hydroxymethylcytosine) from analytes that do not have the feature (e.g., nucleic acids that contain hydroxymethylcytosine). Enrichment typically increases the concentration of the analytes that have the feature (e.g., nucleic acids that contain hydroxymethylcytosine) by at least 2-fold, at least 5-fold or at least 10-fold relative to the analytes that do not have the feature. After enrichment, at least 10%, at least 20%, at least 50%, at least 80% or at least 90% of the analytes in a sample may have the feature used for enrichment. For example, at least 10%, at least 20%, at least 50%, at least 80% or at least 90% of the nucleic acid molecules in an enriched composition may contain a strand having one or more hydroxymethylcytosines that have been modified to contain a capture tag.

As used herein, the terms "circulating cell-free DNA" and "cell-free DNA" (cfDNA) are used interchangeably to refer to DNA that is circulating in the peripheral blood of a patient. The DNA molecules in cell-free DNA may have a median size that is below 1 kb (e.g., in the range of 50 bp to 500 bp, 80 bp to 400 bp, or 100-1,000 bp), although fragments having a median size outside of this range may be present. Cell-free DNA may contain circulating tumor DNA (ctDNA), i.e., tumor DNA circulating freely in the blood of a cancer patient or circulating fetal DNA (if the subject is a pregnant female). cfDNA can be highly fragmented and in some cases can have a mean fragment size about 165-250 bp (Newman et al Nat Med. 2014 20: 548-54). cfDNA can be obtained by centrifuging whole blood to remove all cells, and then isolating the DNA from the remaining plasma or serum. Such methods are well known (see, e.g., Lo et al, Am J Hum Genet 1998; 62:768-75). Circulating cell-free DNA is double-stranded, but can be made single-stranded by denaturation. The term "tagging" as used herein, refers to the appending of a molecular barcode onto a nucleic acid molecule. The molecular barcode may be added to the 5' end, the 3' end, or to both ends of a nucleic acid molecule. Molecular barcodes are typically added to a DNA fragment by ligating an adapter to the fragment using conventional means, e.g., with T4 DNA ligase or another ligase.

The term "molecular barcode" refers to identifier sequences of various types, and encompasses sample identifier sequences, molecule identifier sequences, strand identifier sequences, and other types of identifier sequences as will be discussed herein. In some embodiments, a molecular barcode may have a length in the range of from 1 to about 36 nucleotides, e.g., from 4 to 30 nucleotides, 6 to 25 nucleotides, or 8 to 20 nucleotides. In certain cases, the molecular barcode may be error-detecting and/or error-correcting, meaning that even if there is an error (e.g., if the sequence of the molecular barcode is mis-synthesized, mis-read or distorted during any of the various processing steps leading up to the determination of the molecular barcode sequence) then the code can still be interpreted correctly. The use of error-correcting sequences is described in the literature (e.g., in U.S. Patent Publication Nos. U.S. 2010/0323348 to Hamati et al. and U.S. 2009/0105959 to Braverman et al., both of which are incorporated herein by reference). In some embodiments, an identifier sequence may be of relatively low complexity (e.g., may be composed of a mixture of 4 to 1024 different sequences), although higher complexity identifier sequences can be used in some cases.

As used herein, the term "correspond to," with reference to a sequence read that "corresponds to" a particular (e.g., the top or bottom) strand of a fragment, refers to a sequence read derived from that strand or an amplification product thereof.

As used herein, the term "1,3-cycloaddition reaction" refers to a 1,3-cycloaddition between an azide and alkyne to form a five membered heterocycle. In some embodiments, the alkyne may be strained (e.g., in a ring such as cyclooctyne) and the cycloaddition reaction is carried out under copper-free conditions. Dibenzocyclooctyne (DBCO) and difluorooctyne (DIFO) are examples of alkynes that can participate in a copper-free cycloaddition reaction, although other groups are also known. See, e.g., Kolb et al. (2008) Drug. Discov. Today 8:1128-113); Baskin et al. (2007) Proc. Natl. Acad. Sci. 104:16793-16797; and Sletten et al. (2011) Accounts of Chemical Research 44: 666-676.

The term "click chemistry" refers to a reaction between two or more reactants that spontaneously occurs to form at least one reaction product containing at least one newly formed covalent bond. The 1,3-cycloaddition reaction between an azide an alkyne is an example of a click chemistry type of reaction.

As used herein, the term "UDP glucose modified with a chemoselective group" refers to a uridine diphosphoglucose molecule that has been functionalized, particularly at the 6-hydroxyl position, with a functional group capable of reaction with an affinity tag via click chemistry.

The term "oxidized 5-methylcytosine" refers to an oxidized 5-methylcytosine residue that has been oxidized at the 5-position. Oxidized 5-methylcytosine residues thus include 5-hydroxymethylcytosine, 5-formylcytosine, and 5-carboxylcytosine. The oxidized 5-methylcytosine residues that undergo reaction with an organic borane according to one embodiment of the invention are 5-formylcytosine and 5-carboxylcytosine.

The term "substantially" as in, for example, the phrase "substantially free of" a particular moiety refers to a composition containing not more than 10%, preferably not more than 5%, more preferably not more than 1%, of that particular moiety. Other uses of the term "substantially" involve an analogous definition.

Chemical substituent and compound terminology:

As used herein, the phrase "having the structure" is not intended to be limiting and is used in the same way that the term "comprising" is commonly used.

The term "alkyl" as used herein refers to a branched or unbranched saturated hydrocarbon group typically although not necessarily containing 1 to about 12 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl, and the like. The term "lower alkyl" intends an alkyl group of 1 to 6 carbon atoms. Preferred lower alkyl substituents contain 1 to 3 carbon atoms, and particularly preferred such substituents contain 1 or 2 carbon atoms (i.e., methyl and ethyl). "Substituted alkyl" refers to alkyl substituted with one or more substituent groups, and the terms "heteroatom-containing alkyl" and "heteroalkyl" refer to alkyl in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively.

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Preferred aryl groups contain 5 to 24 carbon atoms, more preferred aryl groups contain 5 to 14 carbon atoms, and particularly preferred aryl groups contain 5 to 9 carbon atoms. "Substituted aryl" refers to an aryl moiety substituted with one or more substituent groups, and the terms "heteroatom-containing aryl" and "heteroaryl" refer to aryl substituent in which at least one carbon atom is replaced with a heteroatom, as will be described in further detail infra. If not otherwise indicated, the term "aryl" includes unsubstituted, substituted, and/or heteroatom-containing aromatic substituents.

The term "heteroatom-containing" as in a "heteroatom-containing alkyl group" (also termed a "heteroalkyl" group) or a "heteroatom-containing aryl group" (also termed a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur, preferably nitrogen or oxygen. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like.

"Hydrocarbyl" refers to univalent hydrocarbyl radicals containing 1 to about 30 carbon atoms, preferably 1 to about 24 carbon atoms, more preferably 1 to about 18 carbon atoms, most preferably about 1 to 12 carbon atoms, including linear, branched, cyclic, saturated, and unsaturated species, such as alkyl groups, alkenyl groups, aryl groups, and the like. "Substituted hydrocarbyl" refers to hydrocarbyl substituted with one or more substituent groups, and the term "heteroatom-containing hydrocarbyl" refers to hydrocarbyl in which at least one carbon atom is replaced with a heteroatom. Unless otherwise indicated, the term "hydrocarbyl" is to be interpreted as including substituted and/or heteroatom-containing hydrocarbyl moieties.

2. Conversion of Oxidized 5mC Residues to DHU in Cell-Free DNA

In one embodiment, the invention provides a method for converting an oxidized 5-methylcytosine residue in cell-free DNA to a dihydrouracil residue. The method involves reaction of an oxidized 5mC residue selected from 5-formylcytosine (5fC), 5-carboxylcytosine (5caC), and combinations thereof, with an organic borane. The oxidized 5mC residue may be naturally occurring or, more typically, the result of a prior oxidation of a 5mC or 5hmC residue, e.g., oxidation of 5mC or 5hmC with a TET family enzyme (e.g., TET1, TET2, or TET3, as will be discussed infra), or chemical oxidation of 5 mC or 5hmC, e.g., with potassium perruthenate ($KRuO_4$) or an inorganic peroxo compound or composition such as peroxotungstate (see, e.g., Okamoto et al. (2011) Chem. Commun. 47:11231-33) and a copper (II) perchlorate/2,2,6,6-tetramethylpiperidine-1-oxyl (TEMPO) combination (see Matsushita et al. (2017) Chem. Commun. 53:5756-59).

The organic borane may be characterized as a complex of borane and a nitrogen-containing compound selected from nitrogen heterocycles and tertiary amines. The nitrogen heterocycle may be monocyclic, bicyclic, or polycyclic, but is typically monocyclic, in the form of a 5- or 6-membered ring that contains a nitrogen heteroatom and optionally one or more additional heteroatoms selected from N, O, and S. The nitrogen heterocycle may be aromatic or alicyclic. Preferred nitrogen heterocycles herein include 2-pyrroline, 2H-pyrrole, 1H-pyrrole, pyrazolidine, imidazolidine, 2-pyrazoline, 2-imidazoline, pyrazole, imidazole, 1,2,4-triazole, 1,2,4-triazole, pyridazine, pyrimidine, pyrazine, 1,2,4-triazine, and 1,3,5-triazine, any of which may be unsubstituted or substituted with one or more non-hydrogen substituents. Typical non-hydrogen substituents are alkyl groups, particularly lower alkyl groups, such as methyl, ethyl, n-propyl, isopropyl, n-butyl, isobutyl, t-butyl, and the like. Exemplary compounds include pyridine borane, 2-methylpyridine borane (also referred to as 2-picoline borane), and 5-ethyl-2-pyridine. These organic boranes may be represented as

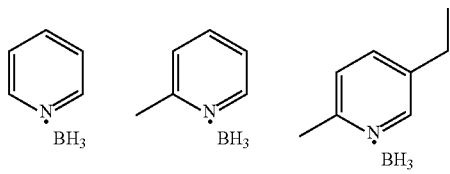

or, as there is evidence of some charge transfer between the heterocyclic nitrogen atom and boron, as

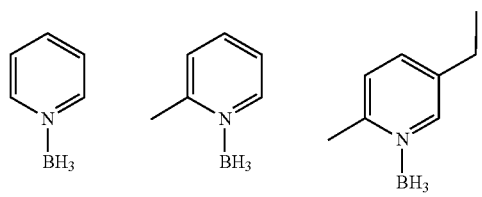

See, e.g., Hoffmann (1964), "Extended Hückel Theory. III. Compounds of Boron and Nitrogen," J. Chem. Phys. 40:2474.

Tertiary amine-borane complexes are formed from borane and a tertiary amine having the structure of formula (I)

in which the $R^1$, $R^2$, and $R^3$ moieties may be the same or different and, generally, are independently selected from $C_1$-$C_{12}$ hydrocarbyl groups, including substituted and/or heteroatom-containing hydrocarbyl groups. $R^1$, $R^2$, and $R^3$ are typically $C_1$-$C_{12}$ alkyl, more typically lower alkyl, such as methyl, ethyl, n-propyl, isopropyl, n-butyl, isobutyl, t-butyl, cyclopentyl, cyclohexyl, and the like. Exemplary tertiary amine-borane complexes for use herein include triethylamine borane and tri(t-butyl)amine borane.

The reaction of the organic borane with the oxidized 5mC residue in cell-free DNA is advantageous insofar as non-toxic reagents and mild reaction conditions can be employed; there is no need for any bisulfite, nor for any other potentially DNA-degrading reagents. Furthermore, conversion of an oxidized 5mC residue to dihydrouracil with the organic borane can be carried out without need for isolation of any intermediates, in a "one-pot" or "one-tube" reaction. This is quite significant, since the conversion involves multiple steps, i.e., (1) reduction of the alkene bond linking C-4 and C-5 in the oxidized 5mC, (2) deamination, and (3) either decarboxylation, if the oxidized 5mC is 5caC, or deformylation, if the oxidized 5mC is 5fC. The sequence of reactions converting 5caC to dihydrouracil using 2-picoline borane as a representative organic borane is illustrated in Scheme 4

Scheme 4

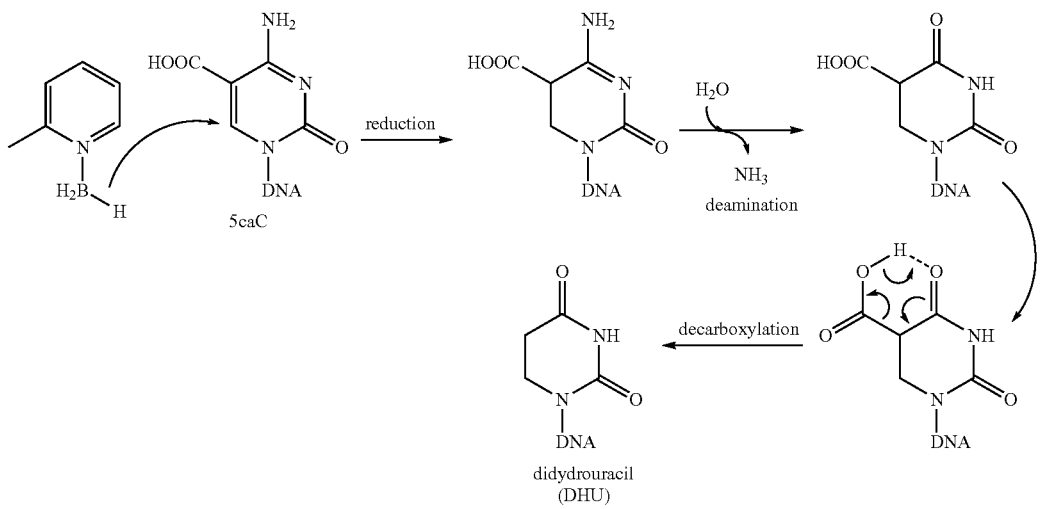

while the corresponding sequence converting 5fC to dihydrouracil is illustrated in Scheme 5

Scheme 5

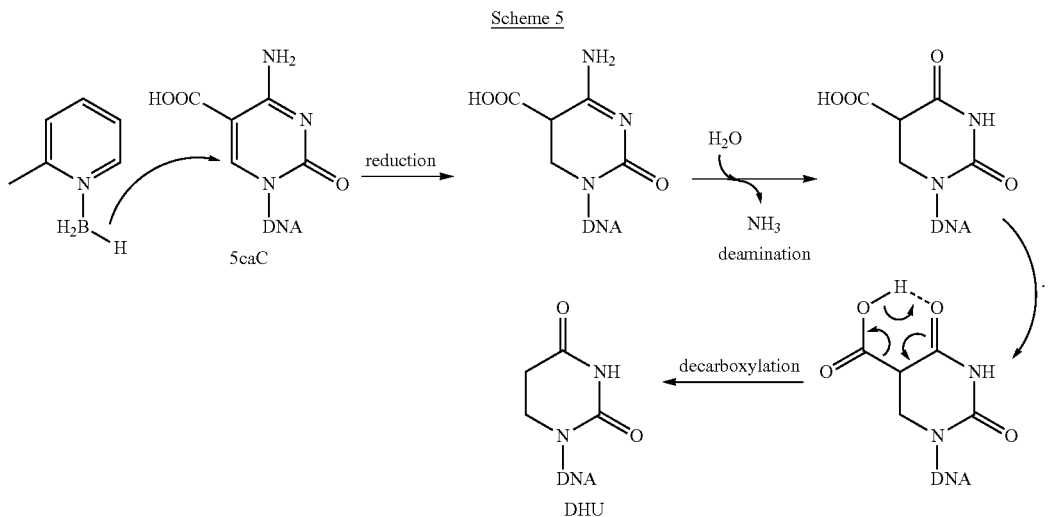

Figure 2:
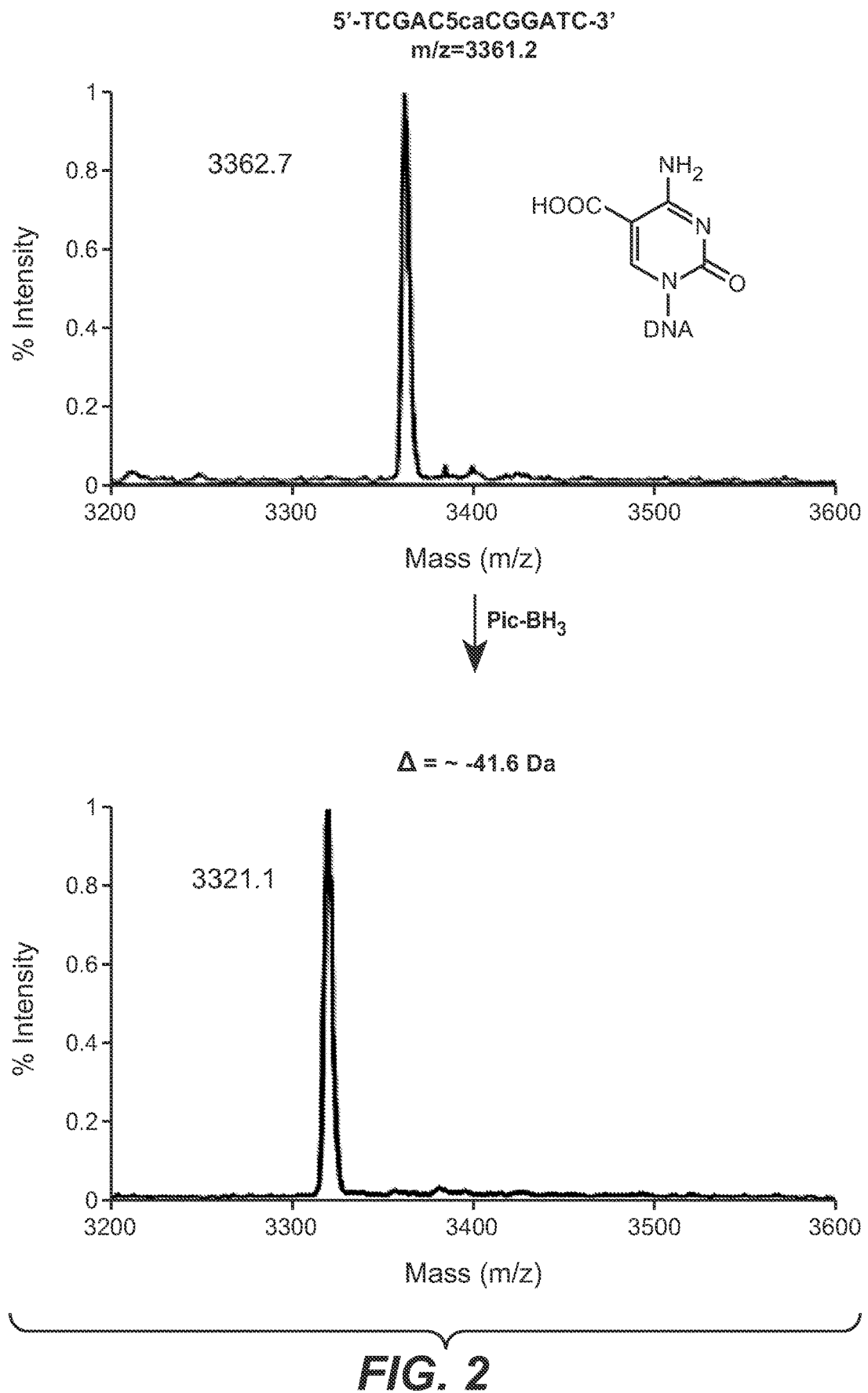
FIG. 2 provides the mass spectra of 5-carboxymethylcytosine (above) and the reaction product of 5-carboxymethylcytosine with 2-picoline borane (Sequence ID NO. 1).
Figure 3A:
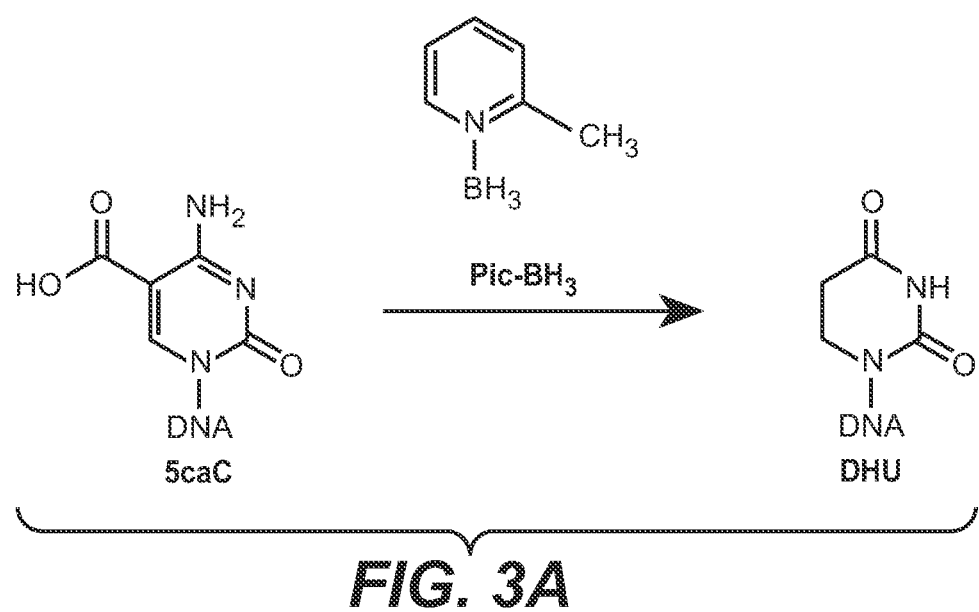
FIG. 3(a), FIG. 3(b) and FIG. 3(c) provides additional spectra confirming the identity of the reaction product of 5-carboxylcytosine with 2-methylpyrimidine as dihydrouracil.
Figure 3B:
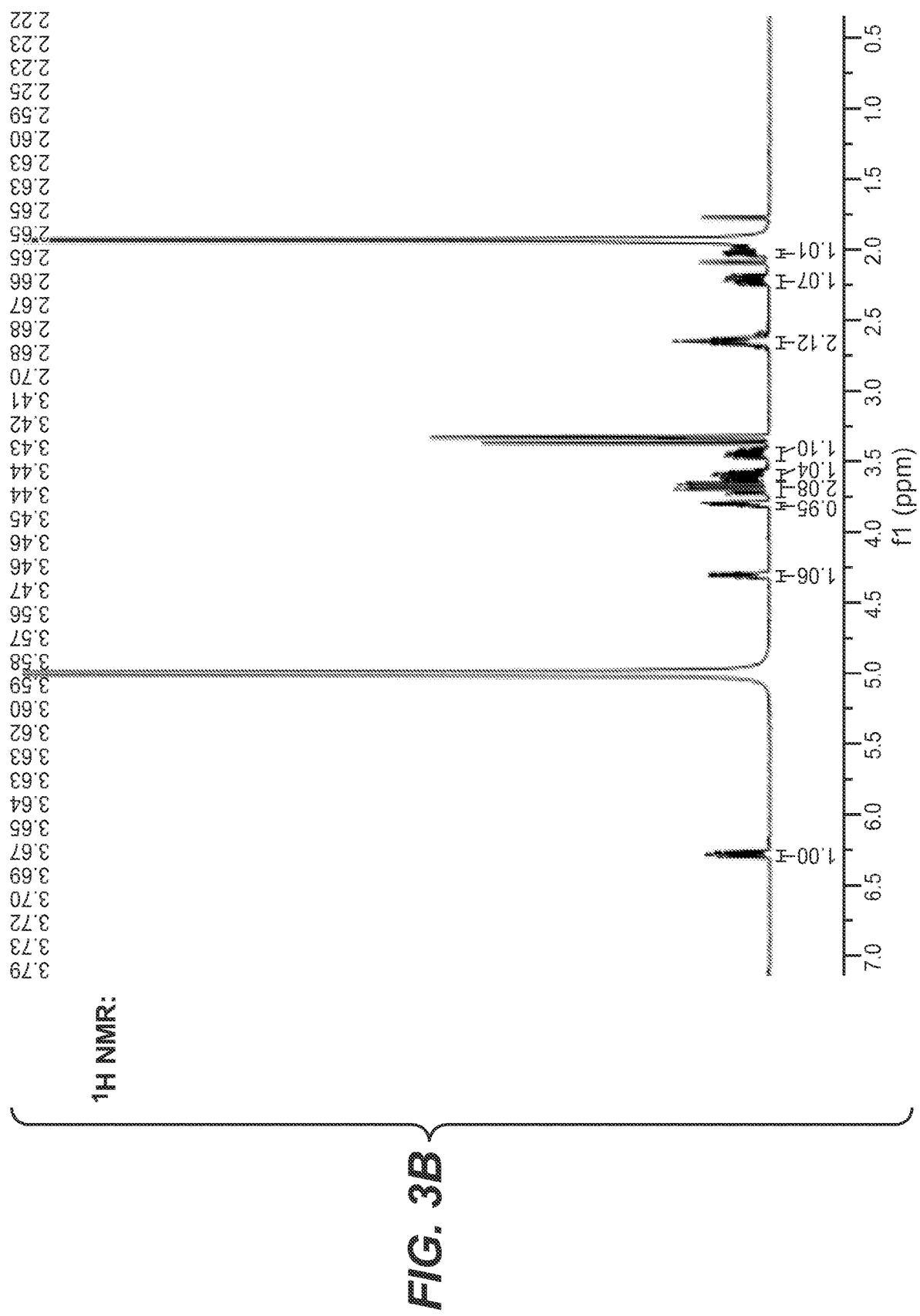
Figure 3C:
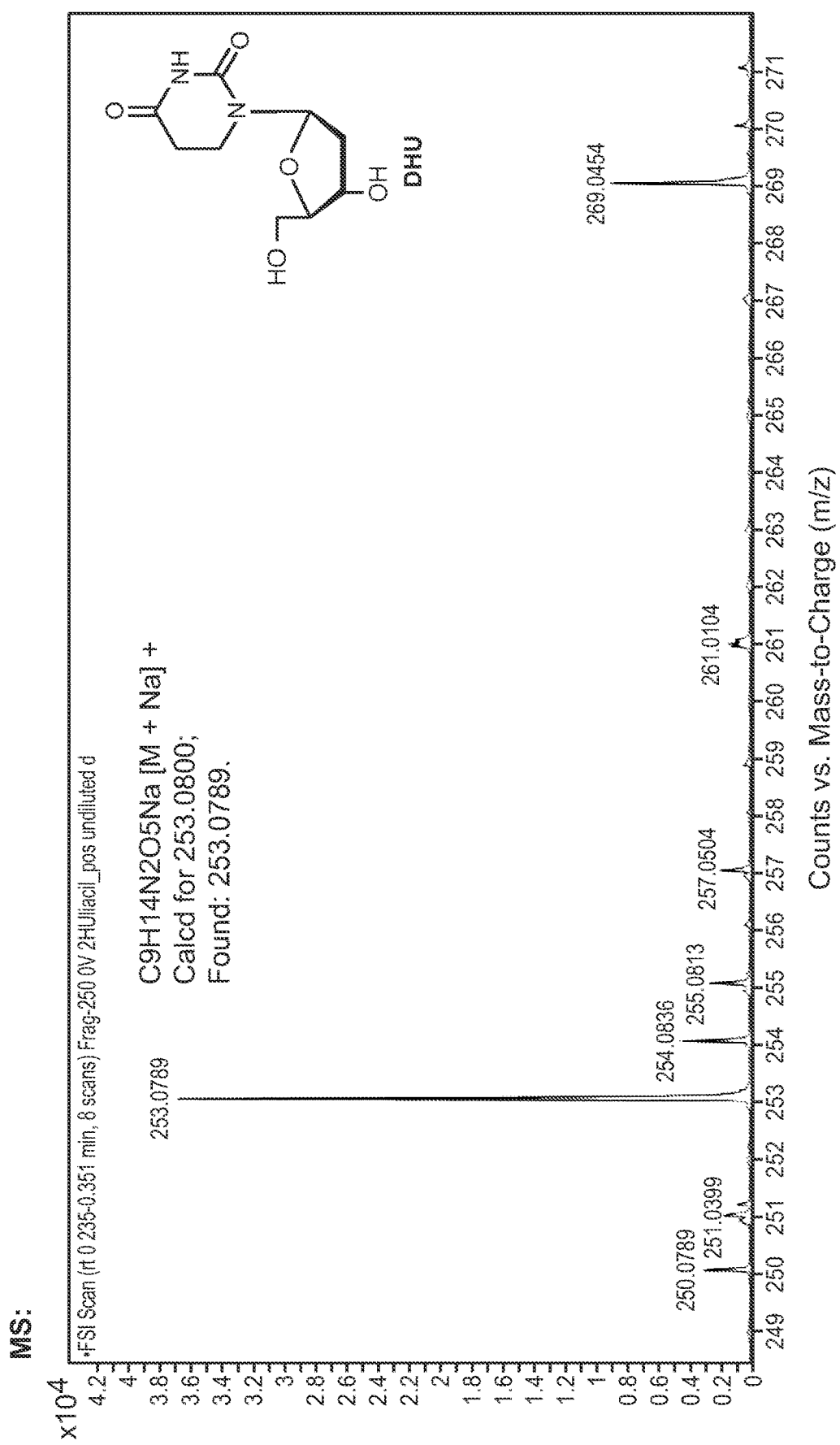
Figure 4:
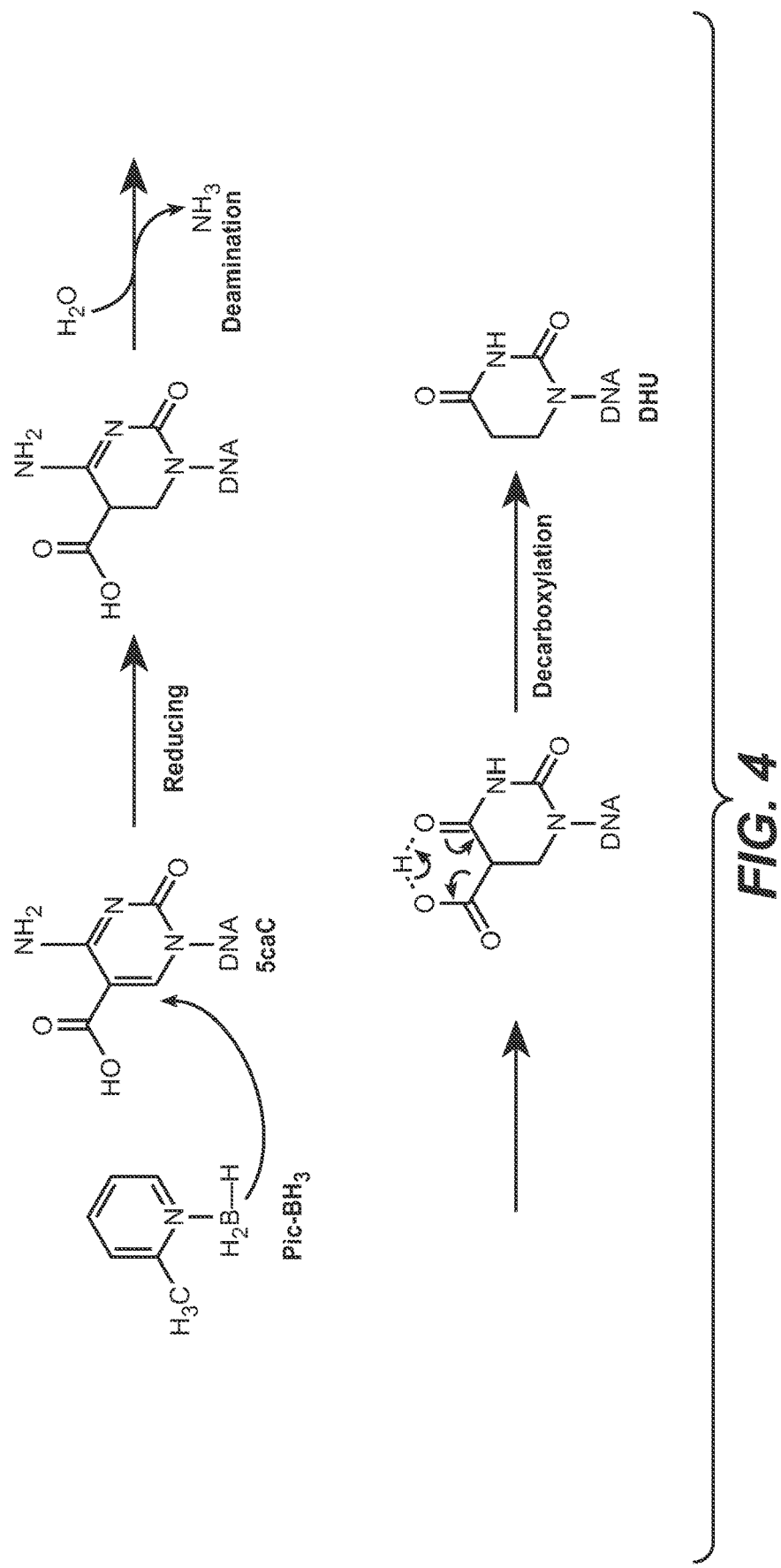
FIG. 4 schematically illustrates the likely reaction mechanism involved in the conversion of 5-carboxylcytosine to dihydrouracil by reaction with 2-picoline borane.
Figure 5:
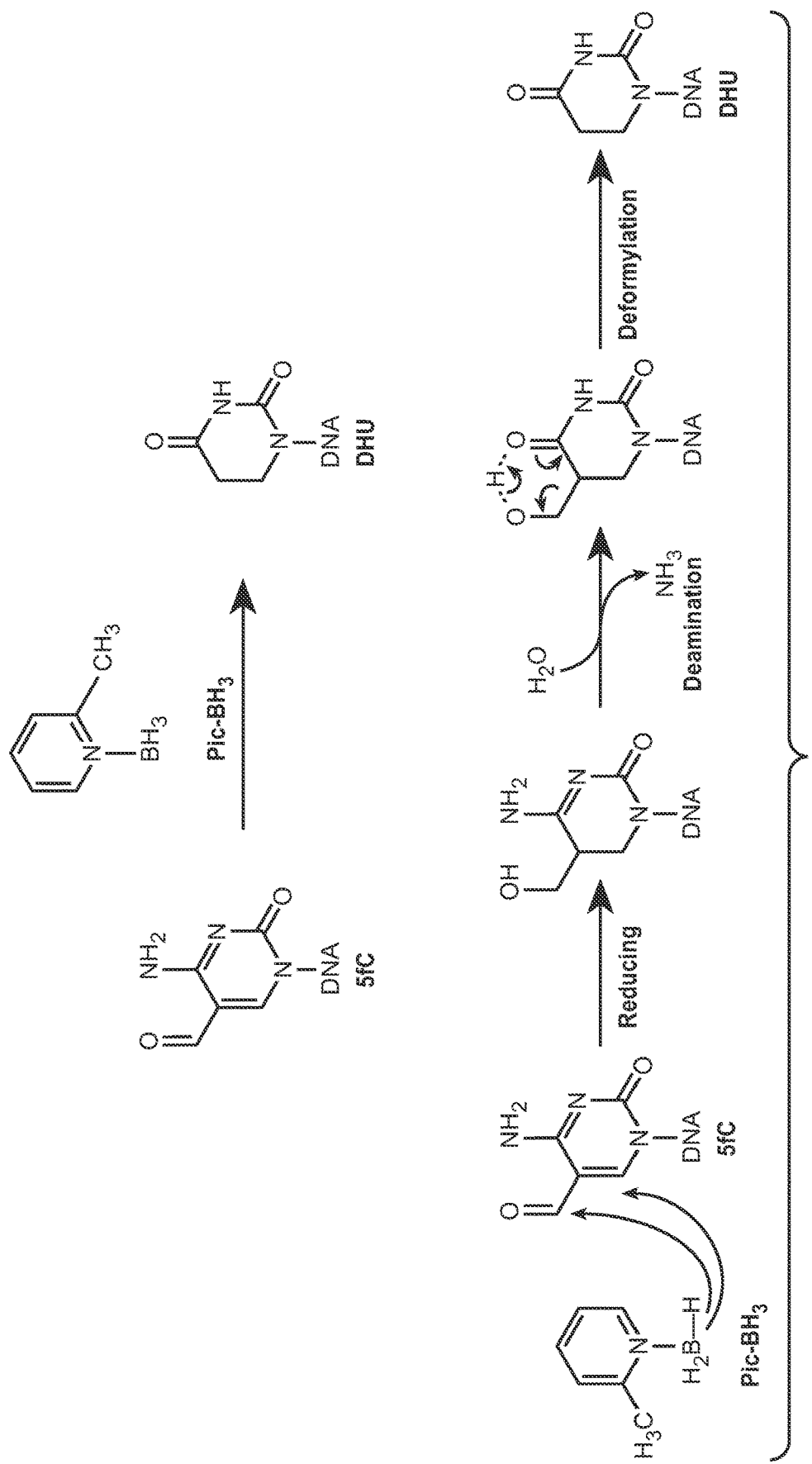
FIG. 5 schematically illustrates the likely reaction mechanism involved in the conversion of 5-formylcytosine to dihydrouracil by reaction with 2-picoline borane borane.

To determine the feasibility of using an organic borane to convert an oxidized 5-methylcytosine residue to dihydrouracil, 2-picoline borane was combined in an aqueous DNA buffer with an oligonucleotide having the sequence 5'-TCGAC5caCGGATC-3', where 5caC represents 5-carboxylcytosine. FIG. 1 illustrates the hypothetical reaction products of 2-picoline borane with 5caC. As indicated, a loss of 41 Da would be expected with dihydrouracil as the reaction product. The results obtained are shown in FIG. 2. A loss of about 41.6 Da was seen, suggesting that the primary reaction product was dihydrouracil. Further $^1$H NMR and mass spectral analysis confirmed this finding; see FIG. 3. The proposed mechanism for the reaction is illustrated schematically in FIG. 4, and involves successive reduction, deamination, and decarboxylation steps as indicated above, while FIG. 5 illustrates the analogous reaction of 2-picoline borane with 5-formylcytosine (5fC). The figure also shows the proposed mechanism, involving successive reduction, deamination, and deformylation.

Figure 6A:
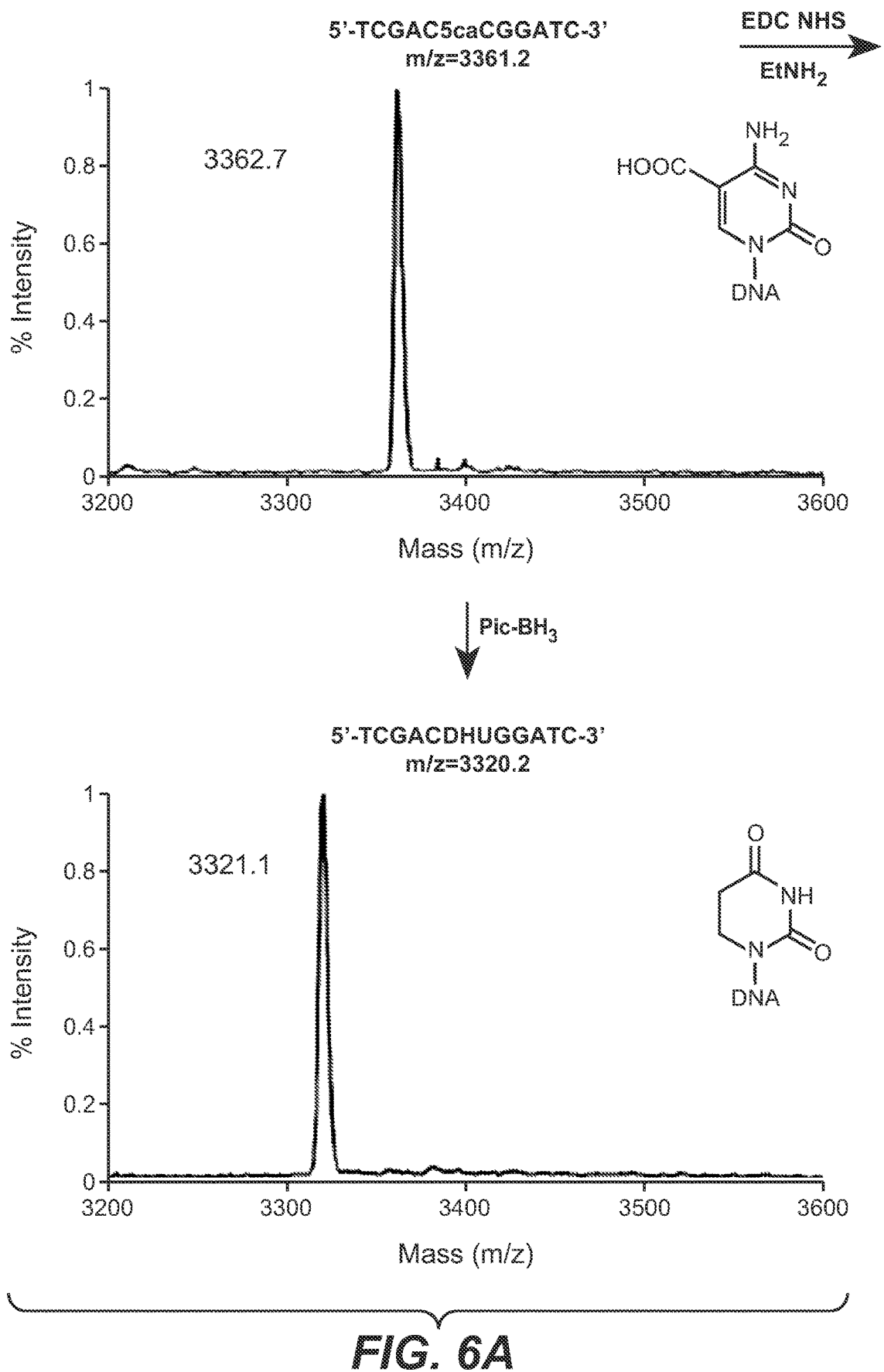
FIG. 6(a), FIG. 6(b), FIG. 7(a) and FIG. 7(b) provide the mass spectra of cytosine substituted at the 5-position with formyl, carboxyl, ethylamido, and ethoxyimino, both before and after reaction with 2-picoline borane (FIGS. 6(a) and (b), Sequence ID NO. 1.
Figure 6B:
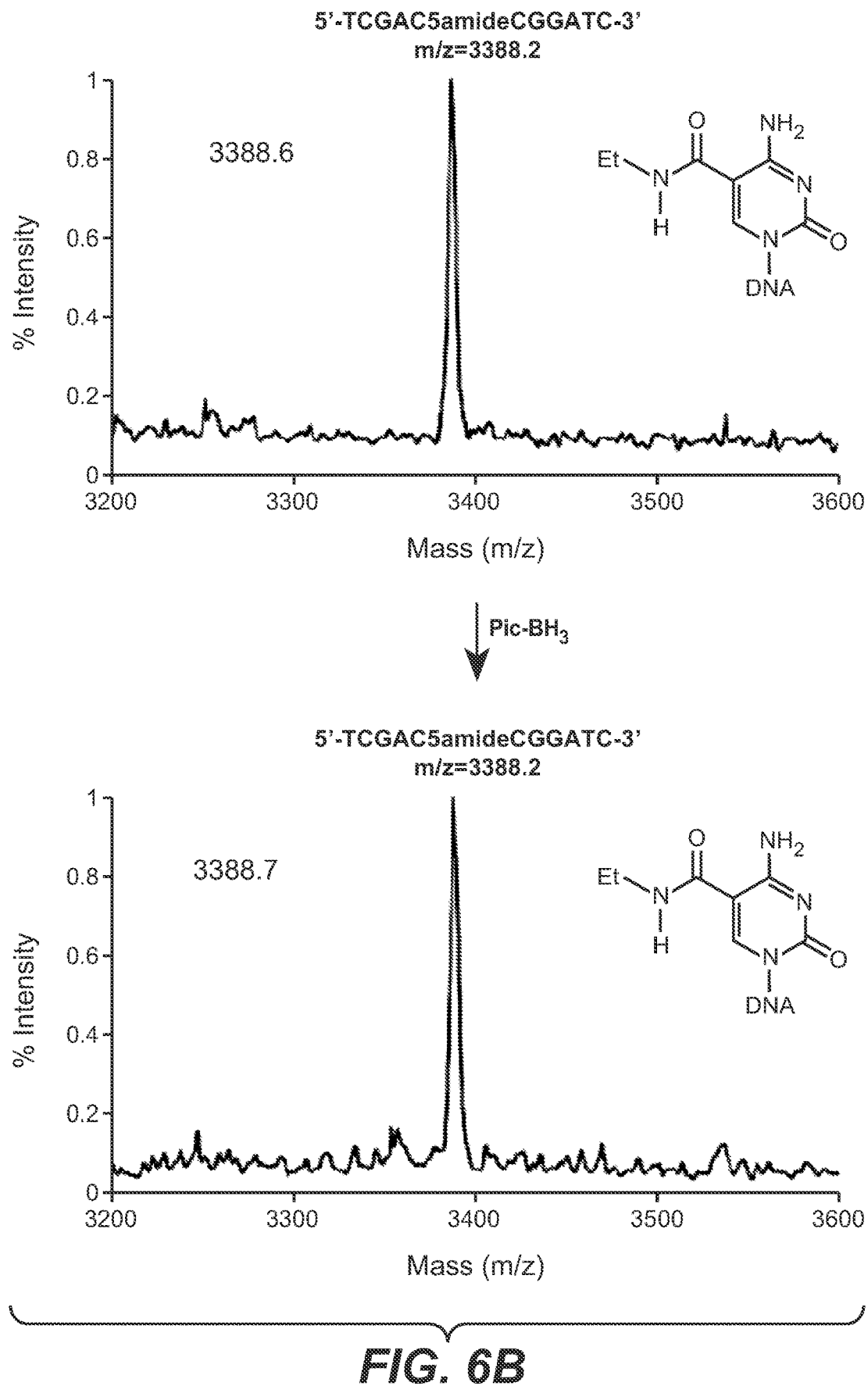
Figure 7A:
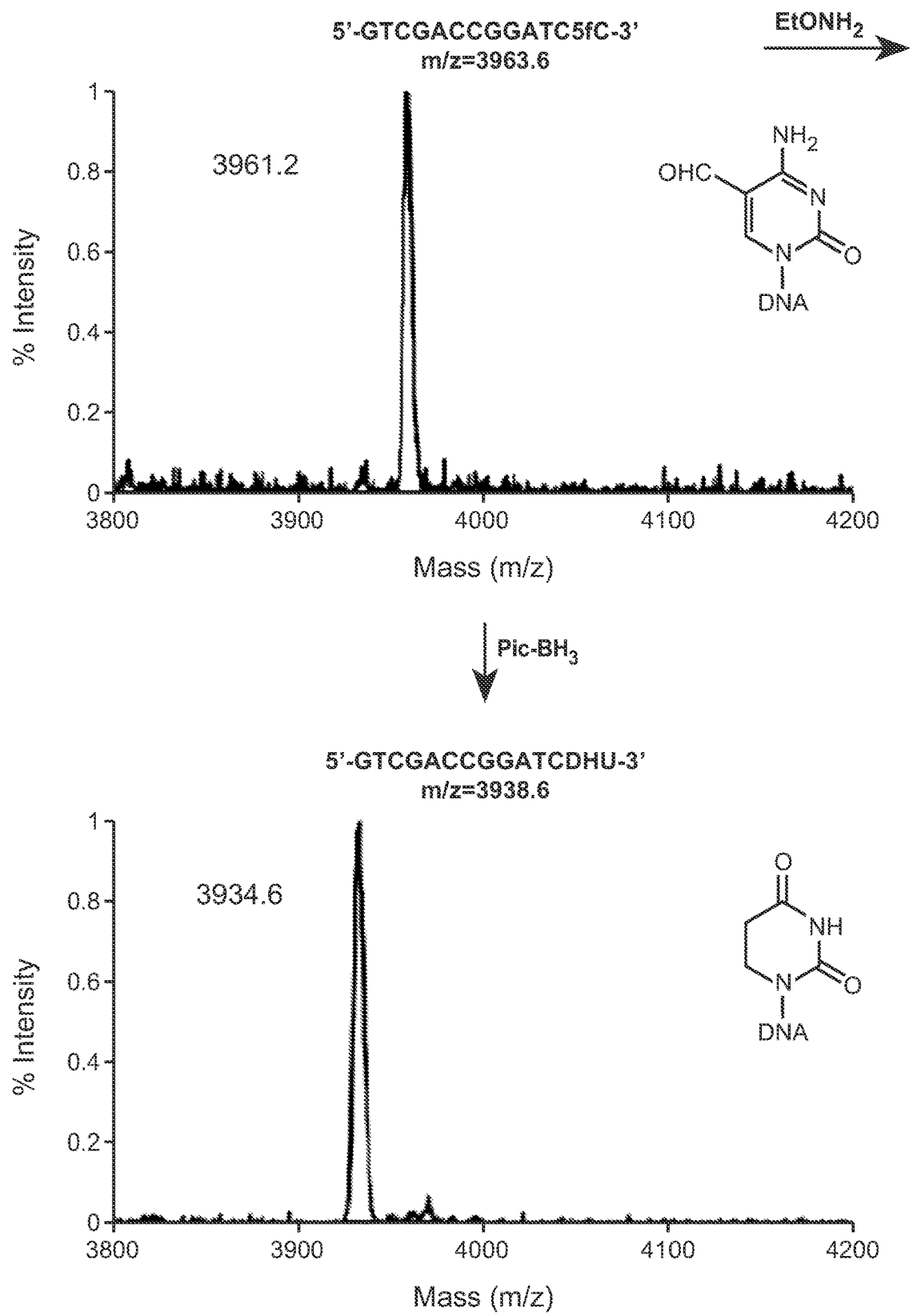
Figure 7B:
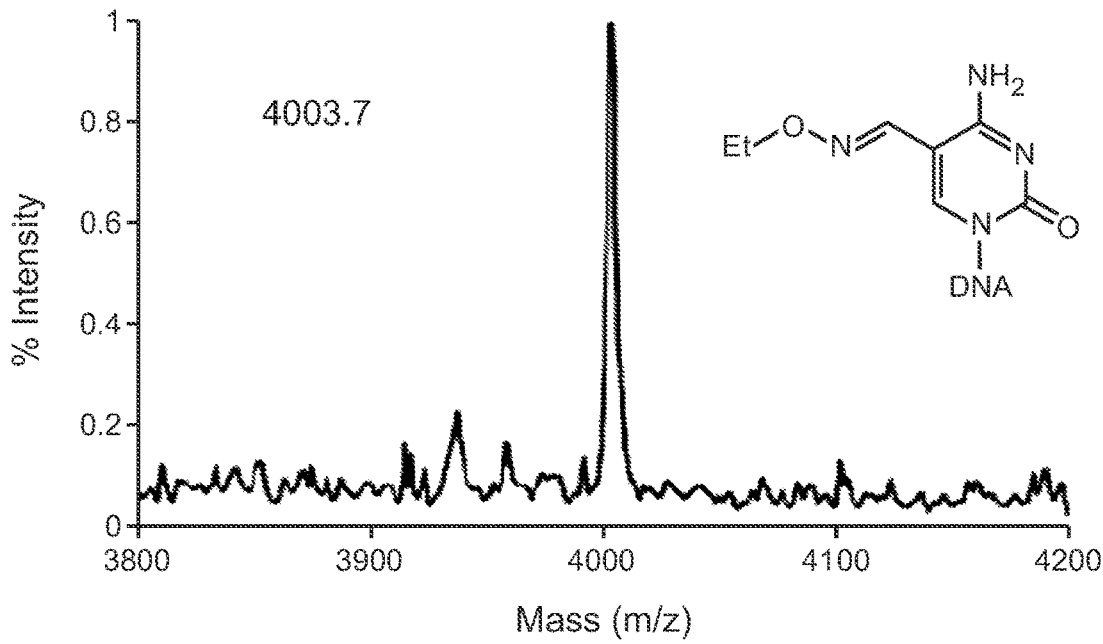
Figure 7B:
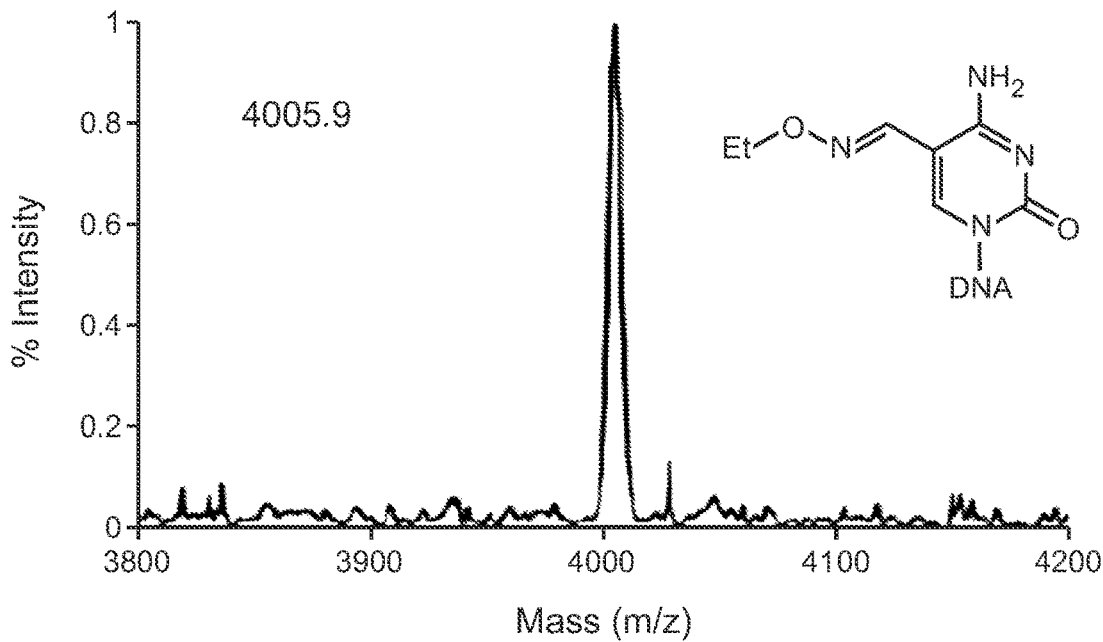

The mass spectra in FIGS. 6 and 7 indicate that 2-picoline borane selectively reacted with 5-carboxylcytosine and 5-formylcytosine to convert those residues to DHU, but does not react with cytosine substituted at the 5-position with the oxime=N—O—CH$_2$CH$_3$ or the amide —(CO)—NH—CH$_2$CH$_3$.

FIG. 10 provides mass spectra of 5-methylcytosine, 5-hydroxymethylcytosine, and 5-glucomethylcytosine, before and after reaction with 2-picoline borane. As may be seen, 2-picoline borane did not react with any of these, highlighting the selectivity of 2-picoline borane for 5-formylcytosine and 5-carboxylcytosine.

In addition to a method for converting an oxidized 5-methylcytosine residue in cell-free DNA to a dihydrouracil residue, the invention also provides a reaction mixture related to the aforementioned method. The reaction mixture comprises a sample of cell-free DNA containing at least one oxidized 5-methylcytosine residue selected from 5caC, 5fC, and combinations thereof, and an organic borane effective to reduce, deaminate, and either decarboxylate or deformylate the at least one oxidized 5-methylcytosine residue. The organic borane is a complex of borane and a nitrogen-containing compound selected from nitrogen heterocycles and tertiary amines, as explained above. In a preferred embodiment, the reaction mixture is substantially free of bisulfite, meaning substantially free of bisulfite ion and bisulfite salts. Ideally, the reaction mixture contains no bisulfite.

In a related aspect of the invention, a kit is provided for converting 5mC residues in cell-free DNA to dihydrouracil residues, where the kit includes a reagent for blocking 5hmC residues, a reagent for oxidizing 5mC residues beyond hydroxymethylation to provide oxidized 5mC residues, and an organic borane effective to reduce, deaminate, and either decarboxylate or deformylate the oxidized 5mC residues. The kit may also include instructions for using the components to carry out the above-described method.

3. Detecting the Presence and Location of 5mC and 5hmC in Cell-Free DNA

In another embodiment, a method is provided that makes use of the above-described oxidation reaction. The method enables detecting the presence and location of 5-methylcytosine residues in cell-free DNA, and comprises the following steps:

(a) modifying 5hmC residues in fragmented, adapter-ligated cell-free DNA to provide an affinity tag thereon, wherein the affinity tag enables removal of modified 5hmC-containing DNA from the cell-free DNA;

(b) removing the modified 5hmC-containing DNA from the cell-free DNA, leaving DNA containing unmodified 5mC residues;

(c) oxidizing the unmodified 5mC residues to give DNA containing oxidized 5mC residues selected from 5caC, 5fC, and combinations thereof;

(d) contacting the DNA containing oxidized 5mC residues with an organic borane effective to reduce, deaminate, and either decarboxylate or deformylate the oxidized 5mC residues, thereby providing DNA containing dihydrouracil residues in place of the oxidized 5mC residues;

(e) amplifying and sequencing the DNA containing dihydrouracil residues;

(f) determining a 5-methylation pattern from the sequencing results in (e).

The cell-free DNA is extracted from a body sample from a subject, where the body sample is typically whole blood, plasma, or serum, most typically plasma, but the sample may also be urine, saliva, mucosal excretions, sputum, stool, or tears. In some embodiments, the cell-free DNA is derived from a tumor. In other embodiments, the cell-free DNA is from a patient with a disease or other pathogenic condition. The cell-free DNA may or may not derive from a tumor. In step (a), it should be noted that the cell-free DNA in which 5hmC residues are to be modified is in purified, fragmented form, and adapter-ligated. DNA purification in this context can be carried out using any suitable method known to those of ordinary skill in the art and/or described in the pertinent literature, and, while cell-free DNA can itself be highly fragmented, further fragmentation may occasionally be desirable, as described, for example, in U.S. Patent Publication No. 2017/0253924 to Lu et al. The cell-free DNA fragments are generally in the size range of about 20 nucleotides to about 500 nucleotides, more typically in the range of about 20 nucleotides to about 250 nucleotides. The purified cell-free DNA fragments that are modified in step (a) have been end-repaired using conventional means (e.g., a restriction enzyme) so that the fragments have a blunt end at each 3' and 5' terminus. In a preferred method, as described in WO 2017/176630 to Quake et al., the blunted fragments have also been provided provided with a 3' overhang comprising a single adenine residue using a polymerase such as Taq polymerase. This facilitates subsequent ligation of a selected universal adapter, i.e., an adapter such as a Y-adapter or a hairpin adapter that ligates to both ends of the cell-free DNA fragments and contains at least one molecular barcode as will be explained in detail infra. Use of adapters also enables selective PCR enrichment of adapter-ligated DNA fragments.

In step (a), then, the "purified, fragmented cell-free DNA" comprises adapter-ligated DNA fragments. Modification of 5hmC residues in these cell-free DNA fragments with an affinity tag, as specified in step (a), is done so as to enable subsequent removal of the modified 5hmC-containing DNA from the cell-free DNA. In one embodiment, the affinity tag comprises a biotin moiety, such as biotin, desthiobiotin, oxybiotin, 2-iminobiotin, diaminobiotin, biotin sulfoxide, biocytin, or the like. Use of a biotin moiety as the affinity tag allows for facile removal with streptavidin, e.g., streptavidin beads, magnetic streptavidin beads, etc.

Tagging 5hmC residues with a biotin moiety or other affinity tag is accomplished by covalent attachment of a chemoselective group to 5hmC residues in the DNA fragments, where the chemoselective group is capable of undergoing reaction with a functionalized affinity tag so as to link the affinity tag to the 5hmC residues. In one embodiment, the chemoselective group is UDP glucose-6-azide, which undergoes a spontaneous 1,3-cycloaddition reaction with an alkyne-functionalized biotin moiety, as described in Robertson et al. (2011) Biochem. Biophys. Res. Comm. 411(1): 40-3, U.S. Pat. No. 8,741,567 to He et al., and WO 2017/176630 to Quake et al., all cited previously. Addition of an alkyne-functionalized biotin-moiety thus results in covalent attachment of the biotin moiety to each 5hmC residue. An example of such a reaction is illustrated in FIG. 5B of U.S. Pat. No. 8,741,567 to He et al., incorporated by reference herein.

The affinity-tagged DNA fragments can then be pulled down in step (b) using, in one embodiment, streptavidin, in the form of streptavidin beads, magnetic streptavidin beads, or the like, and set aside for later analysis, if so desired. The supernatant remaining after removal of the affinity-tagged fragments contains DNA with unmodified 5mC residues and no 5hmC residues.

In step (c), the unmodified 5mC residues are oxidized to provide 5caC residues and/or 5fC residues, using any suitable means. The oxidizing agent is selected to oxidize 5mC residues beyond hydroxymethylation, i.e., to provide 5caC and/or 5fC residues. Oxidation may be carried out enzymatically, using a catalytically active TET family enzyme. A "TET family enzyme" or a "TET enzyme" as those terms are used herein refer to a catalytically active "TET family protein" or a "TET catalytically active fragment" as defined in U.S. Pat. No. 9,115,386, the disclosure of which is incorporated by reference herein. A preferred TET enzyme in this context is TET2; see Ito et al. (2011) Science 333(6047):1300-1303. Oxidation may also be carried out chemically, as described in the preceding section, using a chemical oxidizing agent. Examples of suitable oxidizing agent include, without limitation: a perruthenate anion in the form of an inorganic or organic perruthenate salt, including metal perruthenates such as potassium perruthenate ($KRuO_4$), tetraalkylammonium perruthenates such as tetrapropylammonium perruthenate (TPAP) and tetrabutylammonium perruthenate (TBAP), and polymer supported perruthenate (PSP); and inorganic peroxo compounds and compositions such as peroxotungstate or a copper (II) perchlorate/TEMPO combination. It is unnecessary at this point to separate 5fC-containing fragments from 5caC-containing fragments, insofar as in the next step of the process, step (e) converts both 5fC residues and 5caC residues to dihydrouracil (DHU).

That is, step (e) involves reaction of 5fC-containing and 5caC-containing DNA fragments with an organic borane as described in the preceding section. The organic borane reduces, deaminates, and either decarboxylates or deformylates the oxidized 5mC residues, as illustrated in Scheme 4, Scheme 5, FIG. 4, and FIG. 5. In step (f), the DNA fragments containing DHU in place of the original 5mC residues are pooled, amplified, and sequenced, using any suitable methods; preferred amplification and sequencing techniques herein are described in WO 2017/176630 to Quake et al.

Figure 8A:
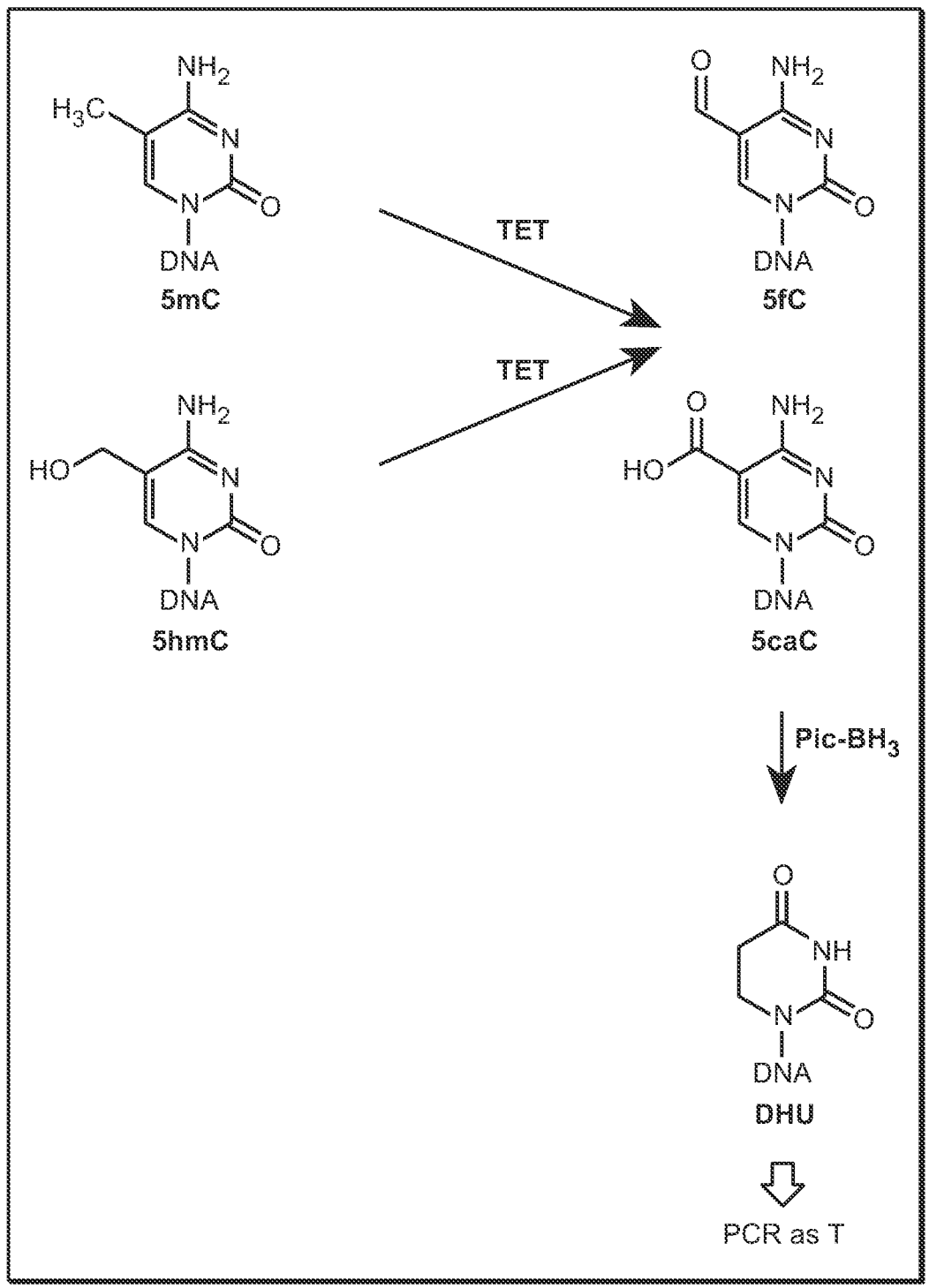
FIG. 8(a) and FIG. 8(b) schematically illustrates methods for the stepwise conversion of 5-methylcytosine and 5-hydroxymethylcytosine to dihydrouracil using an enzymatic oxidizing agent, an optional blocking group, and the organic borane 2-methylpyrimidine borane.
Figure 8B:
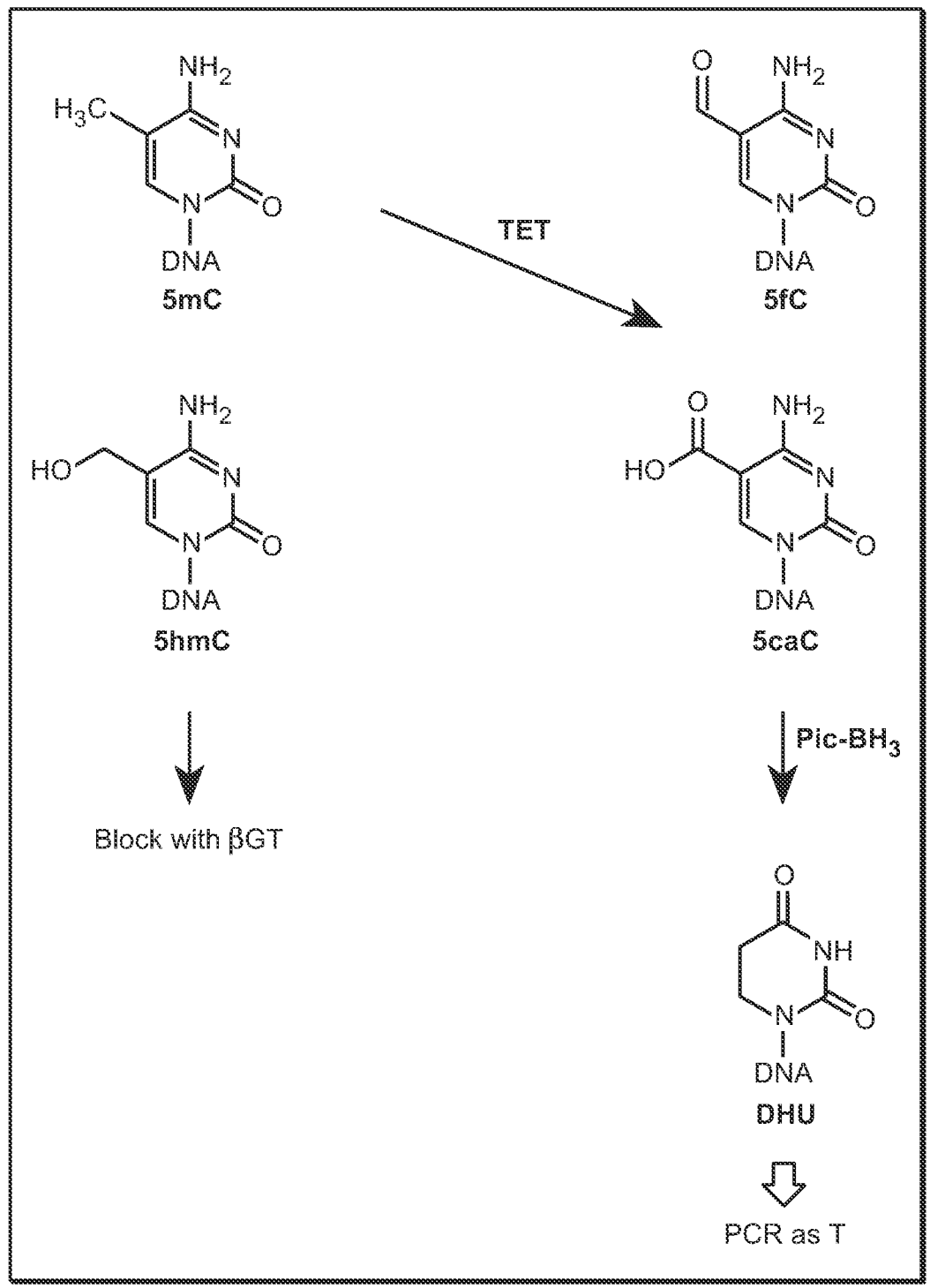
Figure 9:
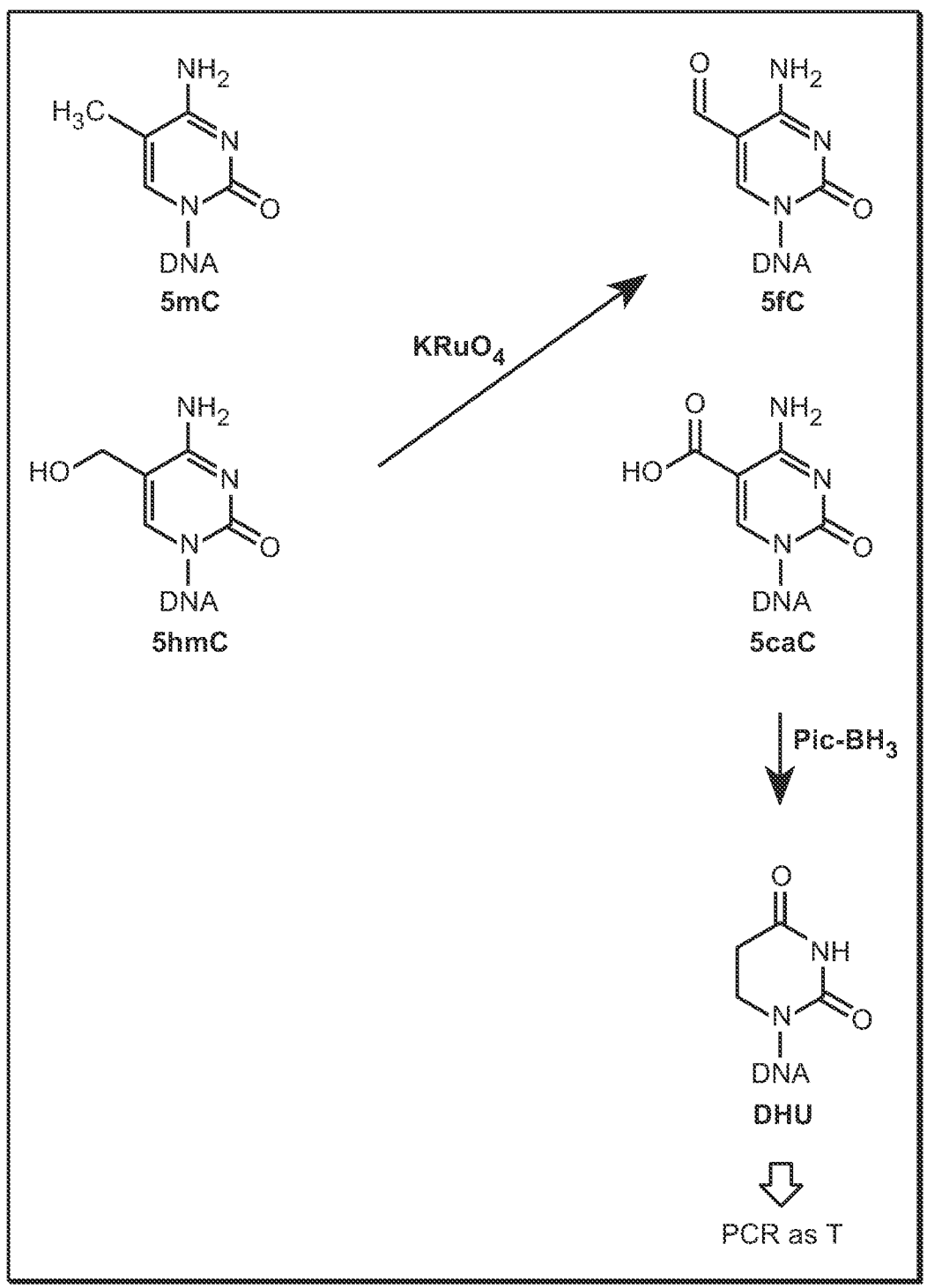
FIG. 9 schematically illustrates a chemical method for the stepwise conversion of 5-hydroxymethylcytosine to dihydrouracil using a chemical oxidizing agent, followed by reaction with the organic borane 2-methylpyrimidine borane.
Figure 10A:
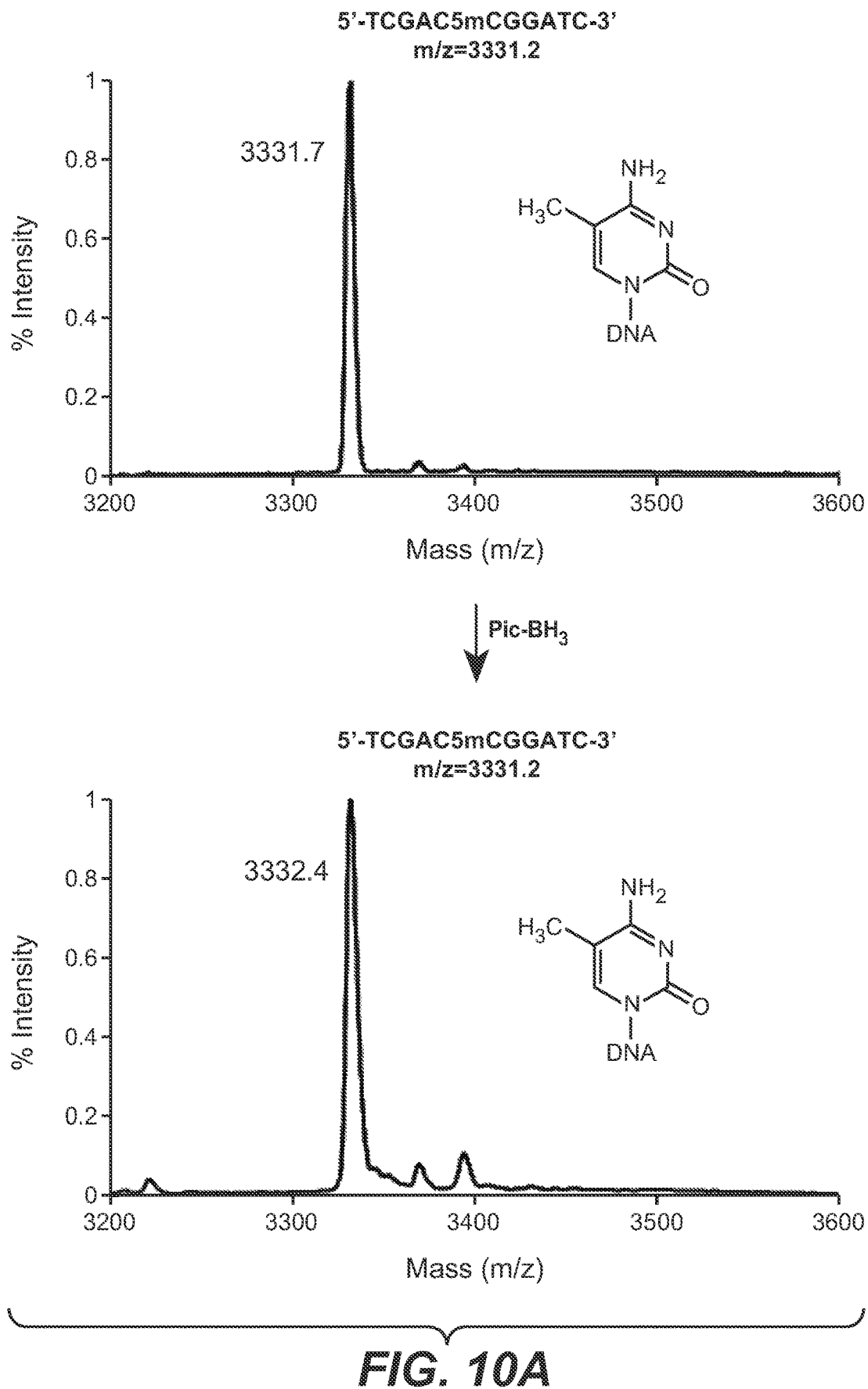
FIG. 10(a), FIG. 10(b) and FIG. 10(c) provides mass spectra of 5-methylcytosine, 5-hydroxymethylcytosine, and 5-glucomethylcytosine, before and after reaction with 2-picoline borane (Sequence ID NO. 1).
Figure 10B:
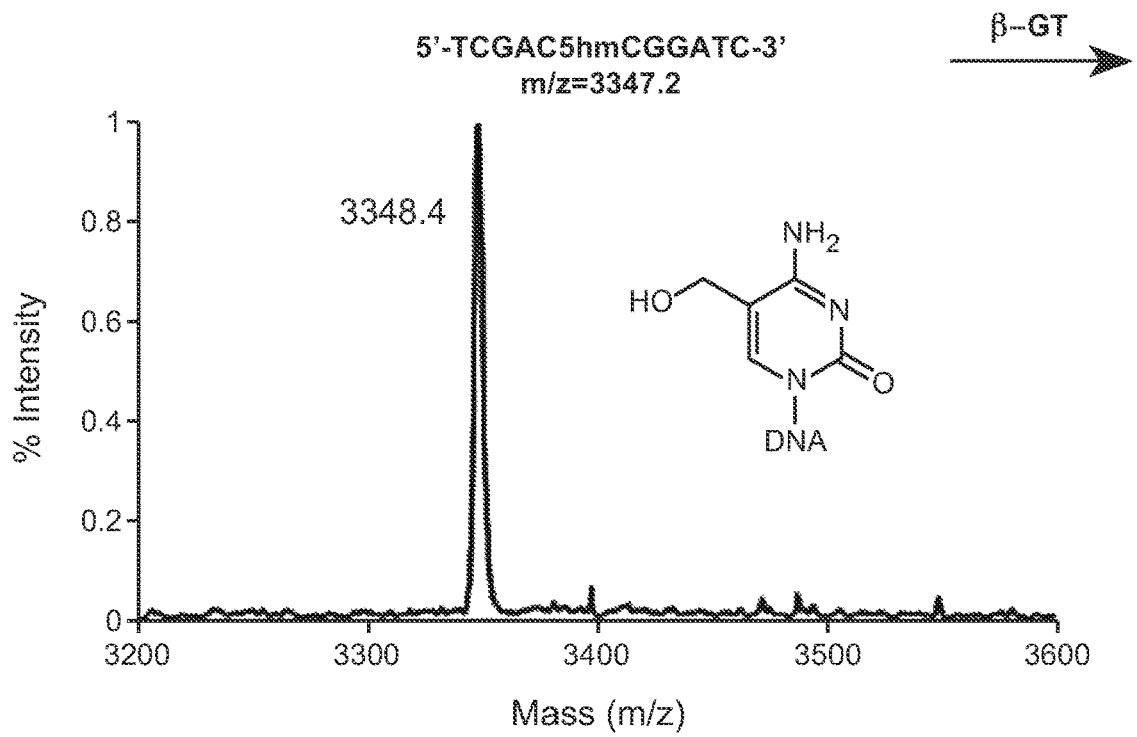
Figure 10B:
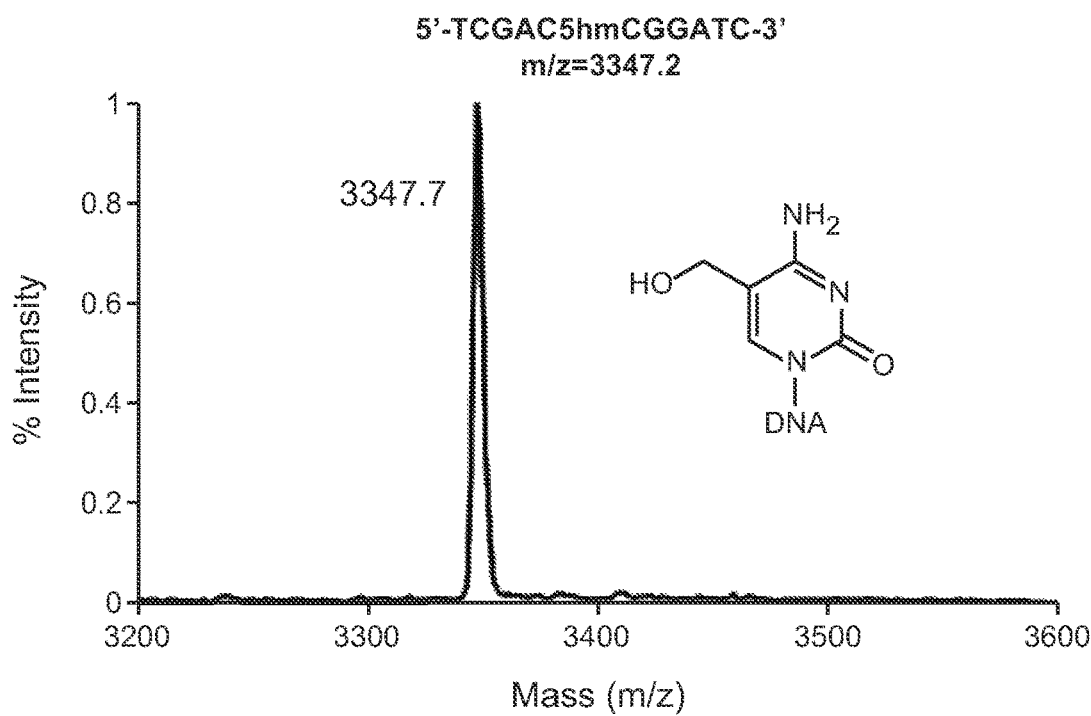
Figure 10C:
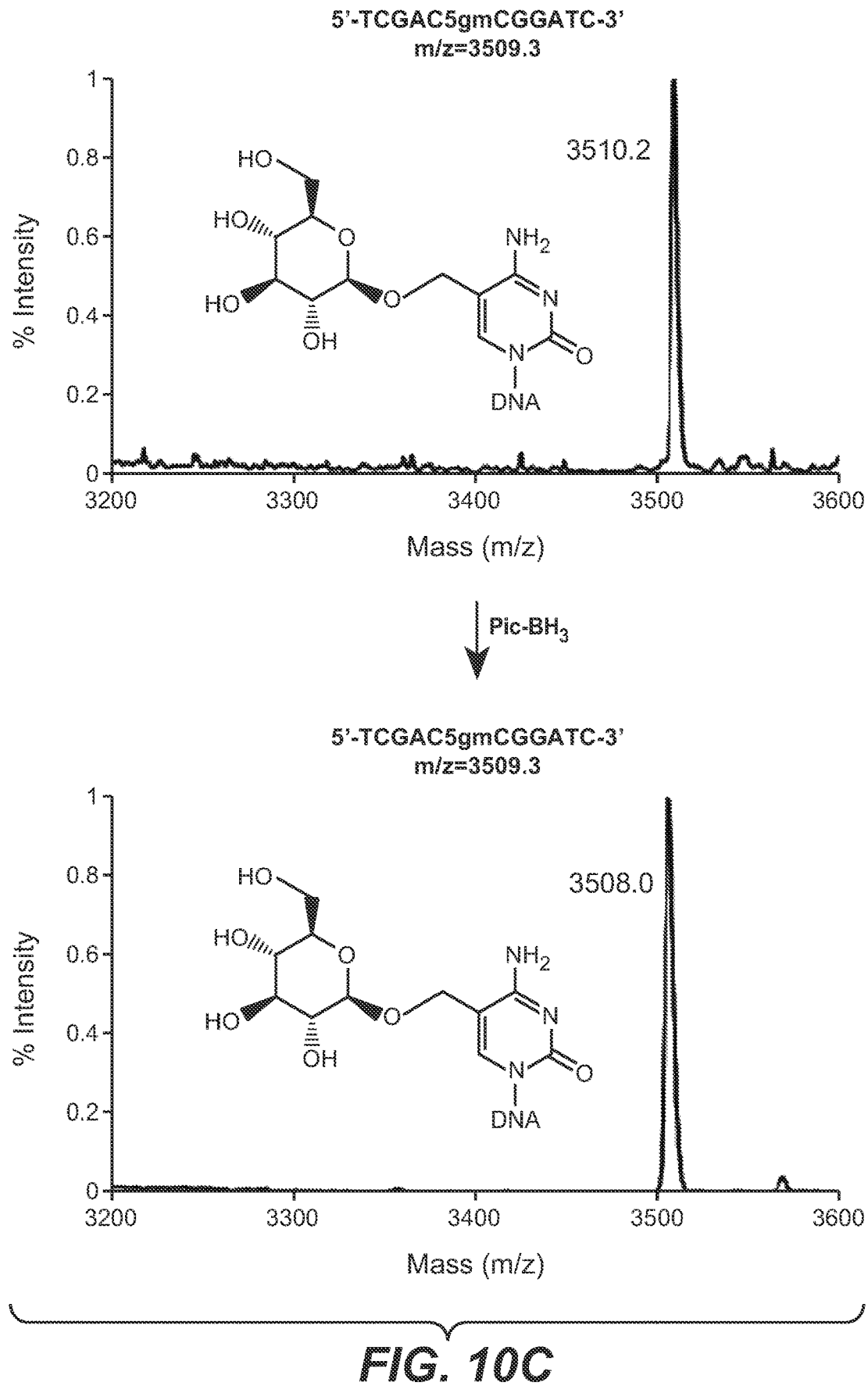

The aforementioned method is illustrated in the scheme at the right-hand side of FIG. 8, and shows TET-assisted 2-picoline borane sequencing (TAPS) with β-GT blocking. The scheme indicates that 5-hydroxymethylcytosine residues are blocked with β-glucosyltransferase (βGT), while 5-methylcytosine residues are oxidized with a TET enzyme effective to provide a mixture of 5-formylcytosine and 5-carboxylcytosine. The mixture containing both of these oxidized species can be reacted with 2-picoline borane or another organic borane to give dihydrouracil. In a variation on this embodiment, 5hmC-containing fragments are not removed in step (b). Rather, as illustrated in the scheme at the left-hand side of FIG. 8, "TET-Assisted Picoline Borane Sequencing (TAPS)," 5mC-containing fragments and 5hmC-containing fragments are together enzymatically oxidized to provide 5fC- and 5caC-containing fragments. Reaction with 2-picoline borane results in DHU residues wherever 5mC and 5hmC residues were originally present. FIG. 9, entitled "Chemical Assisted Picoline Borane Sequencing (CAPS)," schematically illustrates the selective oxidation of 5hmC-containing fragments with potassium perruthenate, leaving 5mC residues unchanged.

The sequence reads of cytosine and the cytosine derivatives 5mC and 5hmC using the aforementioned techniques are shown in Table 1:

TABLE 1

| Residue | Standard Sequencing | Bisulfite Sequencing | Oxidative Bisulfate Sequencing | TAPS (FIG. 8) | TAPS with βGT Blocking (FIG. 8) | CAPS (FIG. 9) |
|---|---|---|---|---|---|---|
| C | C | T | T | C | C | C |
| 5mC | C | C | C | T | T | C |
| 5hmC | C | C | T | T | C | T |

As the table indicates, TAPS with βGT blocking of 5hmC residues and CAPS allow for differential reads of 5mC and 5hmC residues.

There are numerous advantages to the method of this embodiment: bisulfite is unnecessary, nontoxic reagents and reactants are employed; and the process proceeds under mild conditions. In addition, the entire process can be performed in a single tube, without need for isolation of any intermediates.

In a related embodiment, the above method includes a further step: (g) identifying a hydroxymethylation pattern in the 5hmC-containing DNA removed from the cell-free DNA in step (b). This can be carried out using the techniques described in detail in WO 2017/176630 to Quake et al., previously cited and incorporated by reference. The process can be carried out without removal or isolation of intermediates in a one-tube method, as shown schematically in FIG. 11.

Figure 11:
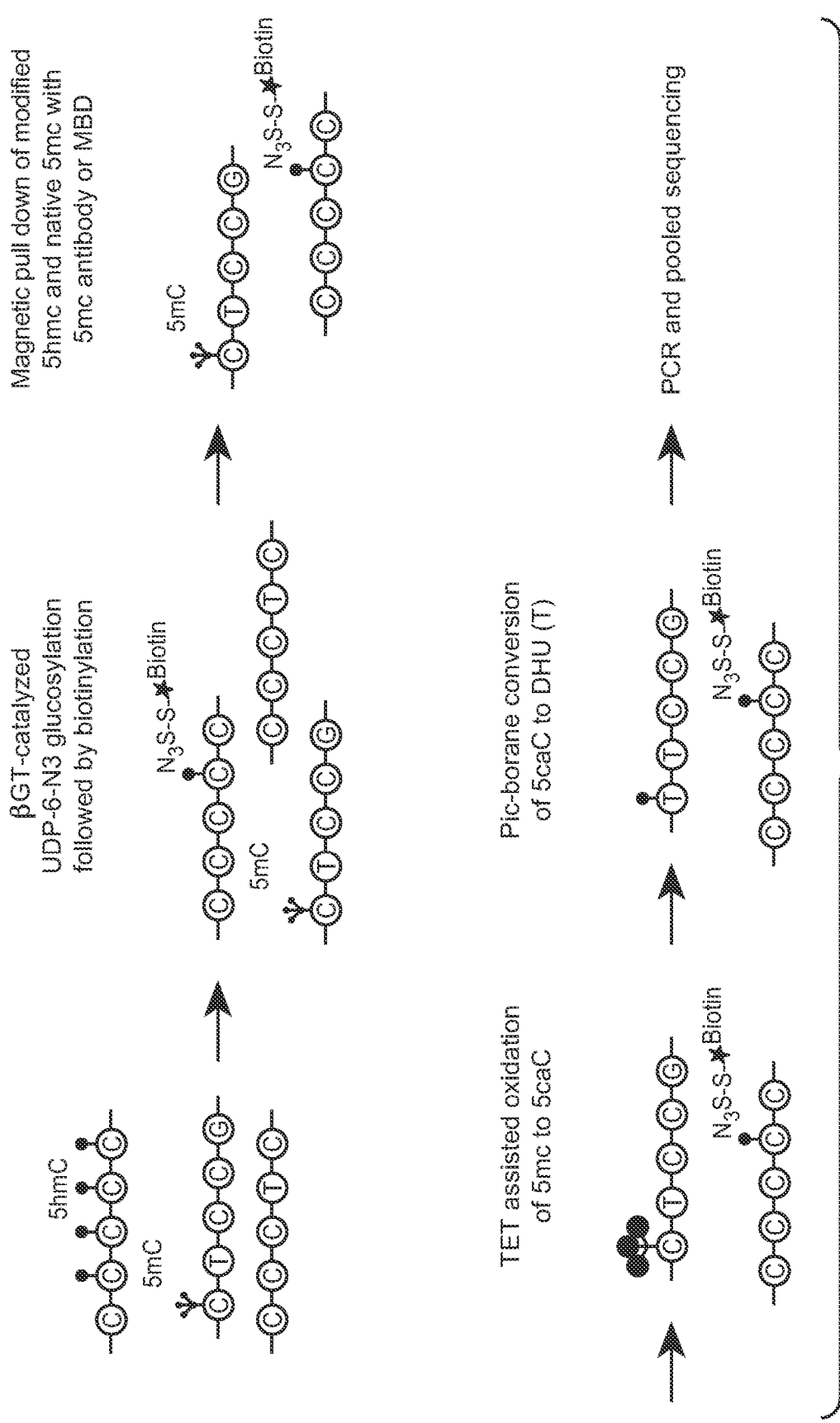
FIG. 11 schematically illustrates one embodiment of a method for detecting the presence and location of 5mC residues in cell-free DNA fragments.

More specifically, FIG. 11 illustrates one embodiment of a method for detecting the presence and location of 5mC residues in cell-free DNA fragments, where the method can be carried out as a "one-tube" process. Initially, cell-free DNA fragments, preferably adapter-ligated DNA fragments, are subjected to functionalization with βGT-catalyzed uridine diphosphoglucose 6-azide as described previously, followed by biotinylation via the chemoselective azide groups. As explained earlier, this procedure results in covalently attached biotin at each 5hmC site. In a next step, the biotinylated strands and strands containing unmodified (native) 5mC are pulled down simultaneously for further processing. The native 5mC-containing strands are pulled down using an anti-5mC antibody or a methyl-CpG-binding domain (MBD) protein, as is known in the art. Then, with the 5hmC residues blocked, the unmodified 5mC residues are selectively oxidized using any suitable technique for converting 5mC to 5fC and/or 5caC, as described elsewhere herein. FIG. 11 refers to one such method, TET-assisted oxidation. An organic borane such as 2-picoline borane is used to convert 5caC to DHU as already described, such that original 5mC residues are read as T residues. For the process of FIG. 11, the single tube sequencing outcomes are as shown in Table 2:

TABLE 2

| Residue | Sequenced as |
|---|---|
| Strand 1 - C | C |
| Strand 2 - G | G |
| Strand 1 - 5mC | T |
| Strand 2 - G | G |
| Strand 1 - 5hmC | C |
| Strand 2 - G | G |

As may be seen in the table, DNA fragments having only 5mC residues (i.e., and no 5hmC residues) are read as TG pairs and thus are uniquely identifiable. If desired, the process can be modified so as to separately pull down the native 5mC-containing fragments and the biotinylated 5hmC fragments, enabling detection of the presence and location of 5hmC residues in the template DNA fragments.

In a variation on the method set forth in steps (a) through (f) and optionally (g), 5hmC residues in the fragmented, adapter-ligated cell-free DNA are modified by attachment of a blocking group, so that the method then proceeds without step (b), removal of 5hmC-containing fragments.

In another variation on the method set forth in steps (a) through (f) and optionally (g), the method is carried out with tumor DNA instead of cell-free DNA.

4. Molecular Barcoding of Cell-Free DNA Fragments

In a preferred embodiment, molecular barcoding is used to identify a feature of each DNA strand in each of a plurality of cell-free DNA samples. A molecular barcode, or "unique identifier" (UID), as explained earlier herein, is a short oligonucleotide sequence that is used to tag or track DNA fragments in order to permit later identification and origin of a particular DNA strand. The molecular barcode, or "sequence tag," thus identifies a feature of the DNA strand to which it is ligated, such as:

(1) the sample from which the DNA strand derived;
(2) the molecule (double-stranded DNA fragment) from which the DNA strand derived;
(3) the identity of the strand in the original double-stranded DNA fragment, i.e., positive or negative; and
(4) an upstream genomic process used to partition an initial pool of nucleic acid template (non-amplified) molecules based on non-sequence characteristics, where "upstream" indicates a process occurring prior to the actual template sequence being read or its presence otherwise detected, for example, by sequencing, e.g., by direct sequencing or pyrosequencing; by hybridization to a complementary sequence, as in a probe or other label; or by sequence specific amplification as in PCR, including methylation-sensitive PCR; by restriction digestion; by MALDI-TOF; using a methylation microarray; and/or by a TAPS or CAPS process as described earlier herein).

In the first instance, the molecular barcode comprises a sample identifier sequence, a sequence of nucleotides that is appended to both strands of a double-stranded DNA fragment, where the sequence identifies the source of the DNA fragment, e.g., the sample and/or patient from which the DNA fragment is derived. In use, each sample is tagged with a different sample identifier sequence, such that one sample identifier sequence is appended to all DNA fragments within one sample, and different sample identifier sequences are used for different samples. After pooling and sequencing, the sample identifier sequence can be used to identify the source of the sequences.

A molecule identifier sequence, the second type of barcode noted above, is a sequence of nucleotides that is appended to both strands of a DNA fragment within a sample, such that the appended sequence of nucleotides, alone or in combination with other features of the fragments, e.g., their fragmentation breakpoints, can be used to distinguish between the different double-stranded fragment molecules in a sample or a portion thereof. The complexity of a population of molecule identifier sequences used in any one implementation may vary depending on a variety of parameters, e.g., the number of fragments in a sample and/or the amount of the sample that is used in a subsequent step. For example, in certain cases, the molecule identifier sequence may be of low complexity (e.g., may be composed of a mixture of 8 to 1024 sequences). In other cases, the molecule identifier sequence may be of high complexity (e.g., may be composed of 1025 to 2M or more sequences). In certain embodiments, a population of molecule identifier sequences may comprise a degenerate base region (DBR) comprising one or more (e.g., at least 2, at least 3, at least 4, at least 5, or 5 to 30 or more) nucleotides selected from R, Y, S, W, K, M, B, D, H, V, N (as defined by the IUPAC code), or a variant thereof. As described in U.S. Pat. No. 8,741,606, a molecule identifier sequence may be made up of sequences that are non-adjacent. In some embodiments, a population of molecule identifier sequences may by made by mixing oligonucleotides of a defined sequence together. In these embodiments, the molecule identifier sequence in each of the oligonucleotides may be error correcting. In the methods described herein, the molecule identifier sequence may be used to distinguish between the different fragments in a portion of an initial sample, where the portion has been removed from the initial sample. The molecule identifier sequences may be used in conjunction with other features of the fragments (e.g., the end sequences of the fragments, which define the breakpoints) to distinguish between the fragments.

A third type of molecular barcode useful in conjunction with the invention is a strand identifier sequence. A strand identifier sequence is specific to one strand of a DNA fragment in a sample, and thus identifies another feature of a sequenced DNA strand, namely, the strand of the original, template DNA fragment from which the sequenced DNA strand derives. In another preferred embodiment, this strand specificity is further enforced by duplex barcoding of each fragment at both ends.

In a preferred embodiment, at least one of the above-described molecular barcodes is used in conjunction with the presently described methods and kits. In a more preferred embodiment, all three types of molecular barcodes are used. In such a case, the three types of barcodes are typically appended to DNA fragments, e.g., in cell-free DNA, by ligating molecular barcode-containing adapters to the end-repaired, A-tailed ends of DNA fragments in a sample. This hybrid adapter approach, analogous to the CAPP-Seq process described by Diehn and Alizadeh in Newman et al. (2016) Nature Biotechnol. and elsewhere, is illustrated in FIG. 12 and FIG. 13.

Figure 12:
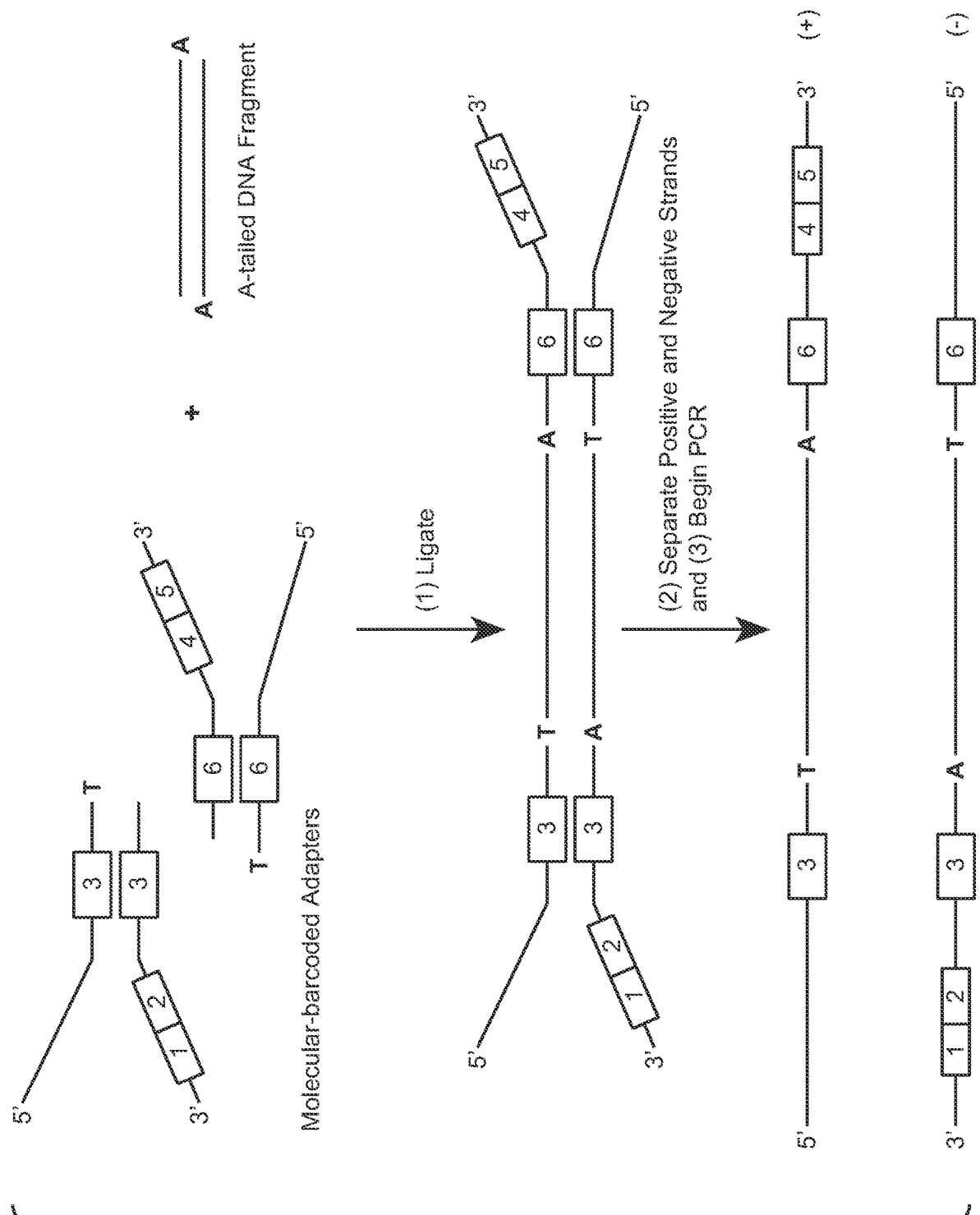
FIG. 12 schematically illustrates the first three steps of a hybrid adapter method for incorporating molecular barcodes into DNA fragments analyzed according to the invention.

The first step of the hybrid adapter methodology, as shown in FIG. 12, is the ligation of the T-terminated molecular-barcoded Y adapters to the A-tailed DNA fragments. While Y adapters are shown, it should be understood that functionally equivalent adapters can also be used, such as the hairpin adapters described earlier. The barcoded adapters each contain the following barcodes: sample identifier sequences 1 and 5; strand identifier sequences 2 and 4; and fragment (or molecule) identifier sequences 3 and 6. Following ligation, positive and negative strands are separated and amplified via PCR (step 3).

Figure 13:
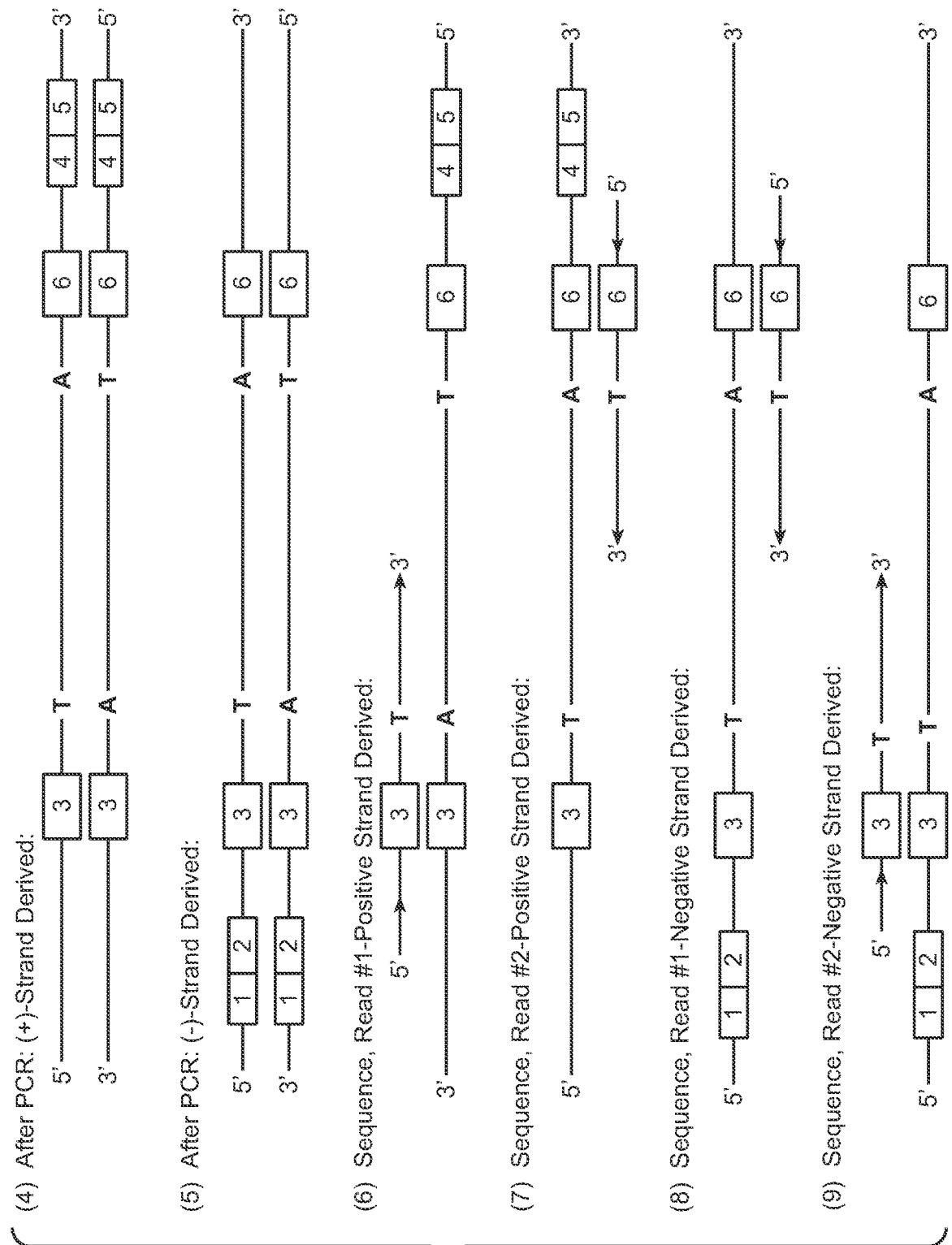
FIG. 13 schematically illustrates the remaining steps of the hybrid adapter method of FIG. 12.

The results of PCR amplification are shown in FIG. 13. The two (+)-strand derived strands are shown at (4), each containing the sample identifier sequence 5, the fragment identifier sequences 3 and 6, and the strand identifier sequence 4. The two (−)-strand derived strands are shown at (5), each containing the sample identifier sequence 1, the fragment identifier sequences 3 and 6, and the strand identifier sequence 2.

In another embodiment, cell-free DNA fragments processed according to the methods herein comprise both a fragment identifier sequence and a strand identifier sequence. Analysis of a strand's fragment identifier sequence (which, again, identifies the template dsDNA fragment from which the processed strand derives) in combination with the strand identifier sequence (identifying the template strand from which the processed strand derives) enables one to determine whether the corresponding template fragment is fully modified (i.e., fully modified, e.g., methylated on both strands, hydroxymethylated on both strands, or methylated on one strand on hydroxymethylated on the other strand) or hemi-modified (i.e., hemi-modified, e.g., methylated or hydroxymethylated on only one strand).

Molecular barcoding can be used in conjunction with any methods described herein. As the present epigenetic analyses, for the most part, rely on cell-free DNA as a starting point, barcoding is normally carried out after purification, fragmentation, and end repair, by ligating barcode-containing adapters to the fragments so processed.

5. Process Barcoding

Molecular barcodes can also be process identifier sequences, as alluded to in the preceding section. Process barcodes, or "process tags," identify a process used to partition an initial pool of non-amplified template DNA fragments based on non-sequence characteristics, such as nucleic acid modifications, association with proteins, and genomic structure.

One advantage of such a process tag is that it converts the non-classical sequence characteristic relating to the original nucleic acid template molecule into a classical sequence difference, thus "immortalizing" such characteristics through subsequent processes which would otherwise mask or destroy said characteristics. For example, modified epigenetic bases such as 5hmC or 5mC on a template molecule would be normally be diluted through rounds of standard PCR or other amplification using the classical four bases, eventually becoming predominantly unmodified cytosine. If instead a process barcode is added as an adjacent sequence to the template molecules processed for such bases prior to amplification, they may be subsequently amplified by normal means and later read (through sequencing or other means such as PCR or microarrays, etc.) together with the template molecule. The presence (or absence) of both the process tag and the template nucleic acid in such reads would therefore indicate whether the original template had such an epigenetic modification, even though subsequent amplification products might not.

A similar case holds for various normal nucleic acid extraction, fragmentation and purification techniques that would normally dissociate the original template nucleic acids from its original binding partners, whether specific proteins (like histones), or adjacent genomic regions spanning outside the sequence of the template molecule itself (for example, CTCF binding sites across genomic spans). Often, immunoprecipitation and nucleic acid crosslinking reactions used to characterize such co-occurrences can only be performed well-upstream of later manipulations or sequence reading or detection. One skilled in the art can recognize that such process barcodes are applicable to any reaction which enables the separation of a pool of nucleic acid into selected and remainder subsets of nucleic acids based upon such characteristics, enabling future marking of the these templates through subsequent reactions, such as extraction, purification, or extraction, which would otherwise remove the original characteristic which had been the basis for such separation (for example, the downstream presence of the binding partner or continued spatial adjacency of other non-contiguous sequences).

Unlike unique molecular identifiers or other highly diverse barcodes (generally in the range of $10^3$ to $10^9$ unique sequences), process barcodes are generally discrete, requiring only a few bases (usually 2-4 bases), thus representing only a few unique sequences (e.g., less than 50, less than 25, less than 20, less than 10 barcode tags, such as one to four barcode tags) that cover the specific outputs of each process. By design, they are applicable to multiple fragments regardless of sequence that are the shared products of the process (sharing a common characteristic used in the process), and validated to be applicable (with acceptable ligation biases) to a large universe of disparate template sequences rather than intended to impart a unique sequence to each individual template molecule. However, they can be added together sequentially, as well as split and re-pooled in combination, in order to cover the many combinations of such processes that run sequentially as a lengthening set of process tag blocks. Different process tags may also be added in parallel processes utilizing individual subfractions of the starting template nucleic acids may be interrogated for different marks. For example, a single template molecule could be tagged with two barcodes indicating its original template molecule also contained both a 5mC and a 5hmC. A further tag may indicate whether the original template molecule also was associated with a particular histone (or modified histone, see, e.g., Shema et al. (2016) Science 352(6286): 717-721, and Sadeh (2016) Molecular Cell 63:1080-1088.

Partitioning of nucleic acids into sub-sets according to this embodiment could be based on the following:

(1) The incorporation of epigenetic bases such as 5hmC or 5mC, which may be chemically modified (such as with bisulfite), labelled or blocked (such as with βGT), or associated with an MBD binding protein;

(2) Association with with specific histones or nucleic acid cross-linking (e.g., CTCF) or binding proteins (such as transcription factors and polymerases, or epigenetic reader and writing proteins) or other nuclear proteins which are typically immunoprecipitated; or (3) Association with geographically near but noncontiguous nucleic acid sequences (typically cross-linked and immunoprecipitated).

The enriched fraction and/or the depleted fraction of a separation can have a process tag added to it. For example, it can be valuable to mark both the fragments containing a modified base with one process tag and the remainder not containing a modified base with another process tag.

The non-sequence modification that is the basis for partitioning is normally contained in a relatively short DNA fragment; while there is utility to detecting more than one non-sequence modification, particularly when such modifications occur in blocks, often it is beneficial to add process tags to smaller nucleic acids that are known from base-resolution analysis to have only a few or one potentially differentially modified sites.

If the fragment size of the template nucleic acid is approximately at or below the modification frequency rate (for example, 1 ever 1000 bases, 1 every 160 bases, or 1 every 100 bases) of the region of the genome being studied (or across the entire genome, if a whole genomic analysis is being performed), individual fragments may become "digital" meaning it will most likely have only one or zero modifications in any given fragment. When the site of the potential modification is known from prior base resolution analyses, a base resolution readout can thus be inferred from a fragment level readout in sequencing.

Figure 14:
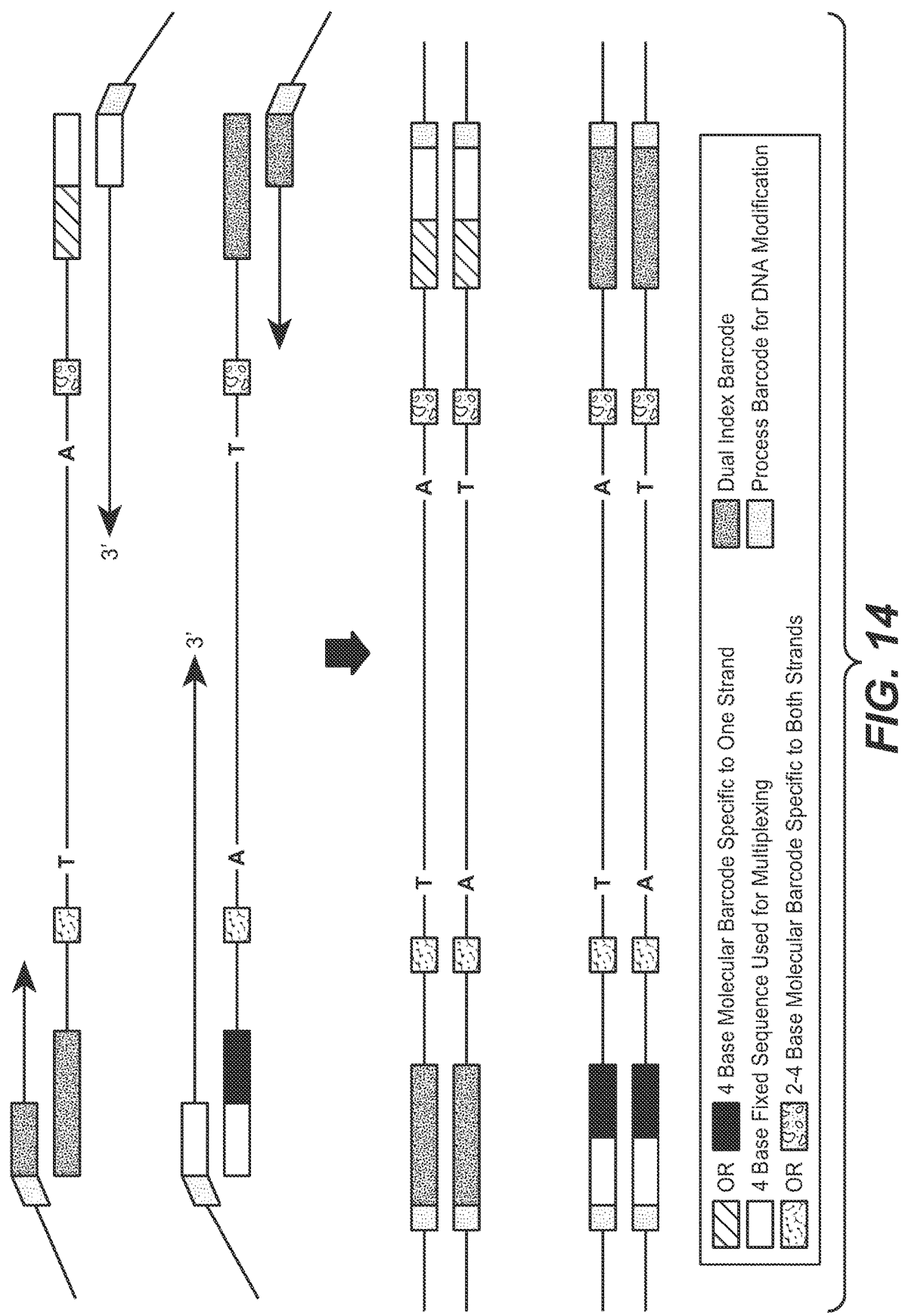
FIG. 14 schematically illustrates a method for incorporating process barcodes to DNA fragments already barcoded with at least one of a sample identifier sequence, a fragment identifier sequence, and a strand identifier sequence.

Process barcodes can be used by themselves or, more preferably, in combination with at least one of the three barcode types addressed in the preceding section. FIG. 14 schematically illustrates the addition of process barcodes to DNA already barcoded with sample identifier sequences, fragment identifier sequences, and strand identifier sequences. Process barcodes are necessarily added to the DNA fragments after strand separation, and preferably during subsequent PCR processing, where the process barcode may be appended to a PCR primer, as shown in FIG. 14.

In one embodiment, use of process barcodes as described is carried out with cell-free DNA and at least one additional molecular barcode selected from sample identifier sequences, fragment identifier sequences, strand identifier sequences, and combinations thereof.

In another embodiment, use of process barcodes as described is carried out with cell-free DNA and no additional barcodes.

In a further embodiment, use of process barcodes is carried out with DNA derived from cellular DNA, and used in conjunction with at least one additional molecular barcode selected from sample identifier sequences, fragment identifier sequences, strand identifier sequences, and combinations thereof.

6. Dual-Biotin Technique for Detecting 5mC and 5hmC in DNA Fragments

As alluded to above, the invention provides methods, reaction mixtures and kits for detecting the presence and location of both 5mC and 5hmC in DNA fragments.

Figure 15:
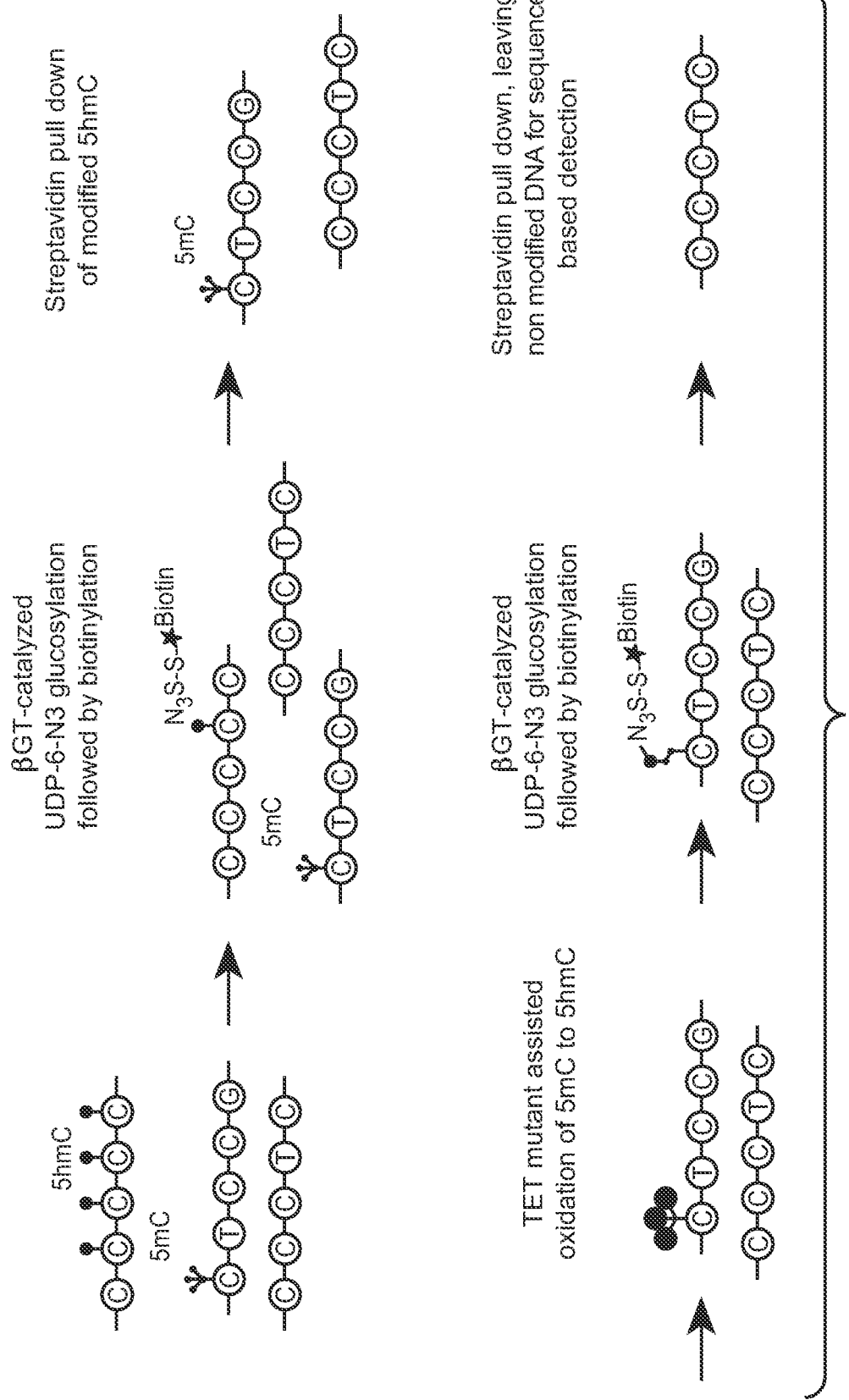
FIG. 15 schematically illustrates the "dual biotin" enrichment method of the invention.

In one embodiment, a "dual biotin" enrichment method is employed to find DNA fragments that either have a 5hmC residue or a 5mC residue. An example of such a method is illustrated in FIG. 15. The method begins with properly adapter-ligated DNA fragments, i.e., adapters that contain one or more molecular barcodes and facilitate selective PCR amplification later in the process. In a first step, 5hmC residues are selectively labeled with an affinity tag. FIG. 15 shows selective functionalization of 5hmC residues via βGT-catalyzed glucosylation with uridine diphosphoglucose-6-azide followed by a "click chemistry" reaction to covalently attach the biotin tag as explained previously. Streptavidin beads are then used to pull out all of the DNA fragments biotinylated at the 5hmC locations, and placed in a separate container for process barcoding during PCR amplification. The remaining DNA fragments in the supernatant are fragments that either have 5mC residues or have no modifications. A TET protein or a TET mutant protein is then used to oxidize 5mC residues in the supernatant to 5hmC; in this case, a mutant TET protein is employed to ensure that oxidation of 5mC does not proceed beyond hydroxylation. Suitable TET mutant protein for this purpose are described in Liu et al. (2017) Nature Chem. Bio. 13: 181-191, and the βGT-catalyzed glucosylation followed by biotin functionalization is then repeated. The fragments so marked—biotinylated at each of the original 5mC locations—are pulled down with streptavidin beads. The bead-bound DNA fragments are then process barcoded—with a different process identifier sequence than used in the first step—during PCR amplification. Unmodified DNA fragments, i.e., fragments containing no modified cytosine residues, now remain in the supernatant. If desired, sequence-specific probes can be used to hybridize to unmethylated DNA strands. The hybridized complexes that result can be pulled out and tagged with a third process barcode during PCR, as before.

The dual biotin enrichment method thus results in three separate groups of cell-free DNA fragments, corresponding to original DNA fragments having 5hmC residues, original DNA fragments having 5mC residues, and original DNA fragments not containing any C modifications. The three groups are pooled and sequenced, with the barcoding enabling bioinformatic deconvolution to determine the structure of the initial DNA fragments.

In a preferred embodiment, the DNA fragments undergoing dual biotin enrichment processing are cell-free DNA fragments.

7. Biotin/Native 5mC Enrichment Method

Figure 16:
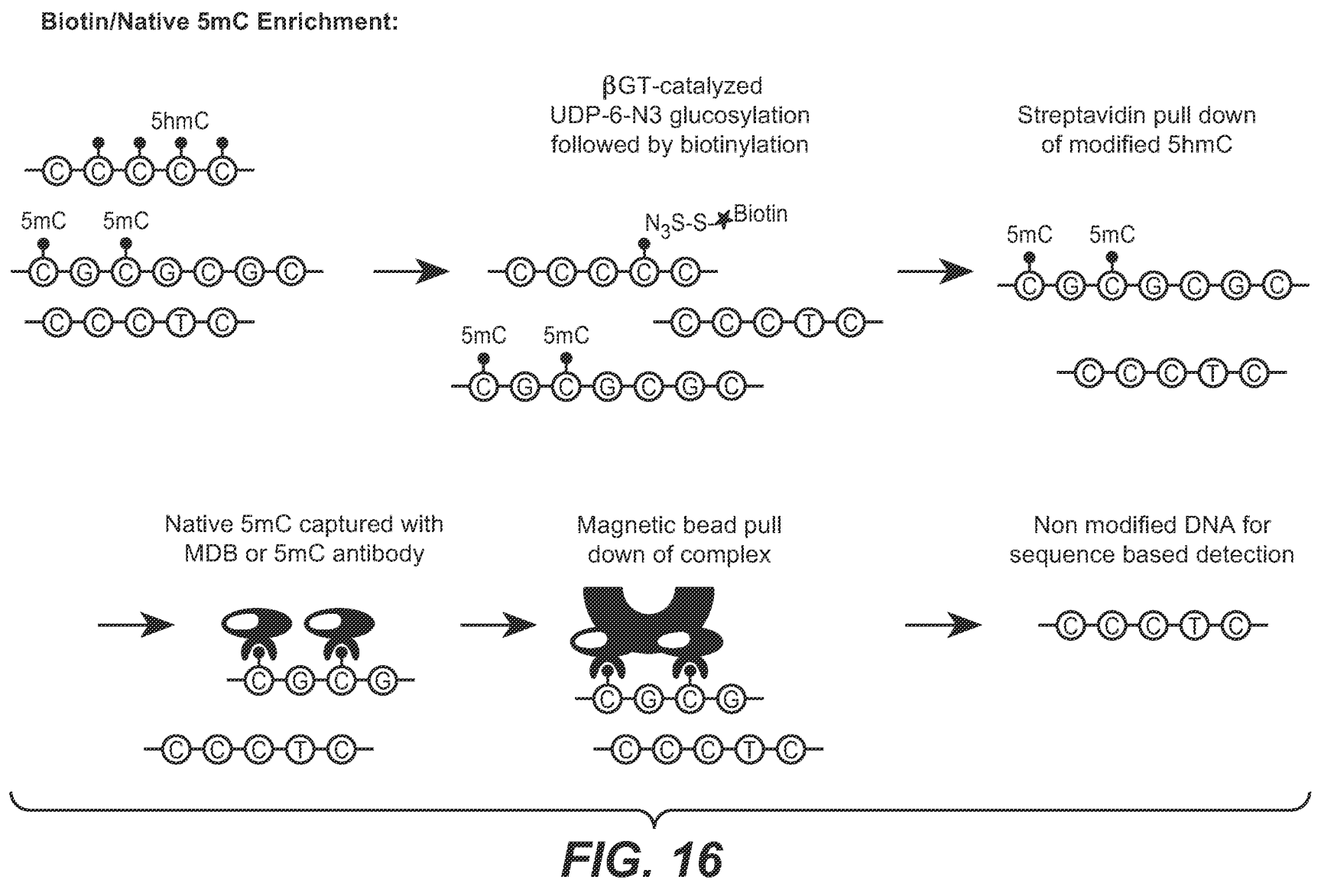

A related embodiment is illustrated in FIG. 16. The method begins as in the preceding section, with biotinylation of 5hmC residues in adapter-ligated DNA fragments, followed by streptavidin pull-down. Here, instead of modifying the methylated DNA that remains, however, an anti-5mC antibody or an MBD protein is used to capture and pull down native 5mC-containing fragments. The remaining unmethylated DNA can be processed as described in the preceding section. The three groups of fragments can be amplified and tagged with process barcodes, pooled, sequenced as above.

8. Identification of 5mC/5hmC Co-Occurrence on a Single DNA Strand

The invention also encompasses a novel method for detecting 5mC and 5hmC residues in DNA fragments, including the identification of DNA fragments in which 5mC and 5hmC are both present on a single strand.

Figure 17:
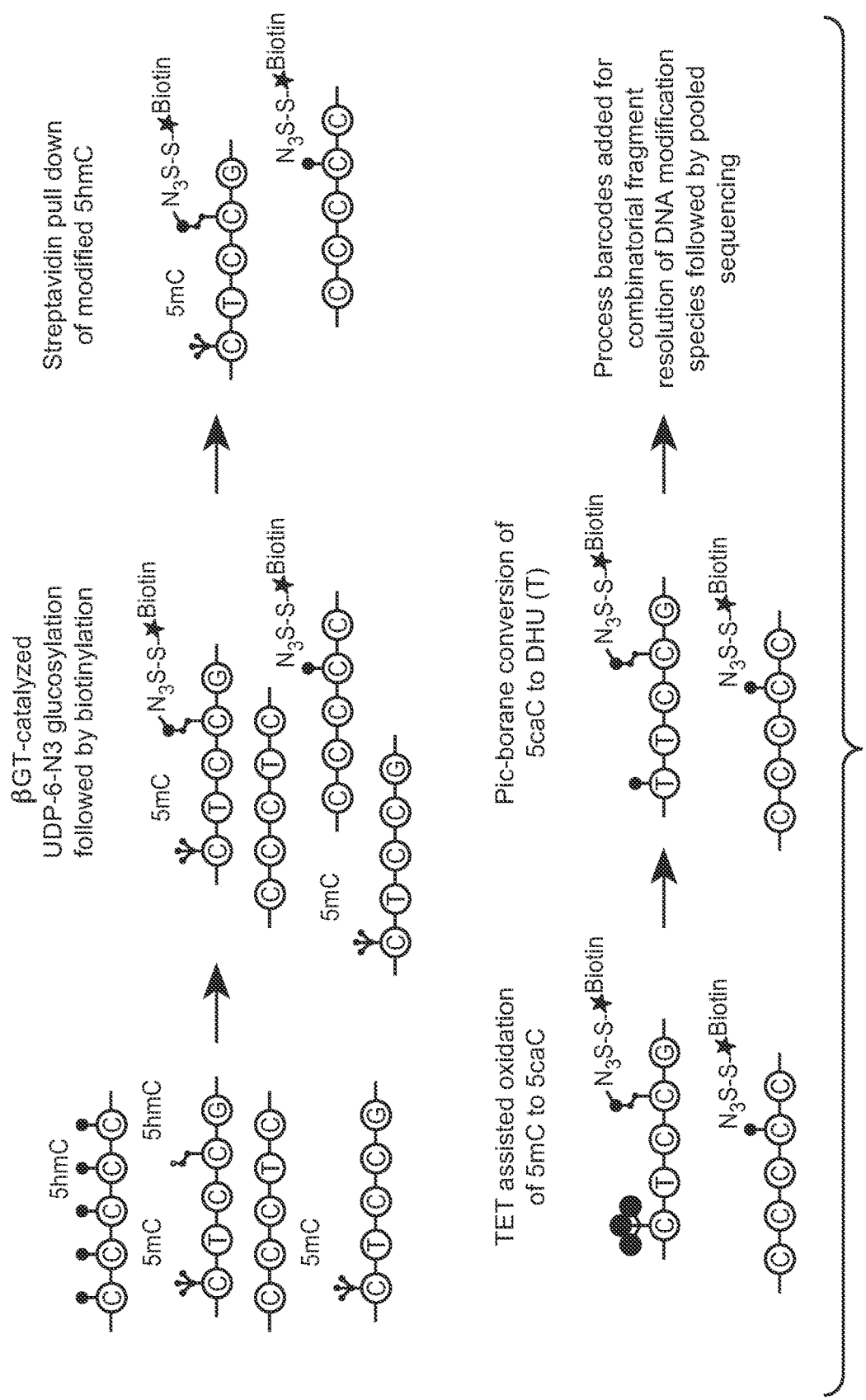
FIG. 17 schematically illustrates a method for identifying DNA fragments in which at least one strand contains both a 5mC and a 5hmC residue.

As before, the first step can be carried out using any method effective to separate out 5hmC-containing DNA fragments that have been adapter ligated. The method involves affixing an affinity tag to the 5hmC sites, e.g., by functionalization of 5hmC with a chemoselective agent, which in turn covalently binds an affinity tag. An example of such a method is illustrated in FIG. 17. In FIG. 17, the adapter-ligated 5hmC-containing fragments are functionalized with azide groups using βGT-catalyzed glucosylation with uridine diphosphoglucose-6-azide followed by attachment of biotin as the affinity tag as described previously. Streptavidin beads are used to pull-down the DNA fragments that have been biotinylated. It will be appreciated that all DNA fragments isolated in this manner have biotinylated 5hmC sites. Some of these fragments may contain unmodified 5mC sites as well. In a next step, the fragments are oxidized as described previously, using a TET enzyme or the like, so that 5mC residues are converted to 5fC and/or 5caC. An organic borane such as 2-picoline borane is used as explained earlier to reduce, deaminate, and either decarboxylate or deformylate the oxidized 5mC moieties to give DHU residues. All DNA fragments processed in this way thus originally included at least one strand containing both a 5mC moiety and a 5hmC moiety. Process barcodes can then be added on during PCR amplification for combinatorial fragment resolution of the DNA modification species, followed by pooled sequencing.

Figure 18:
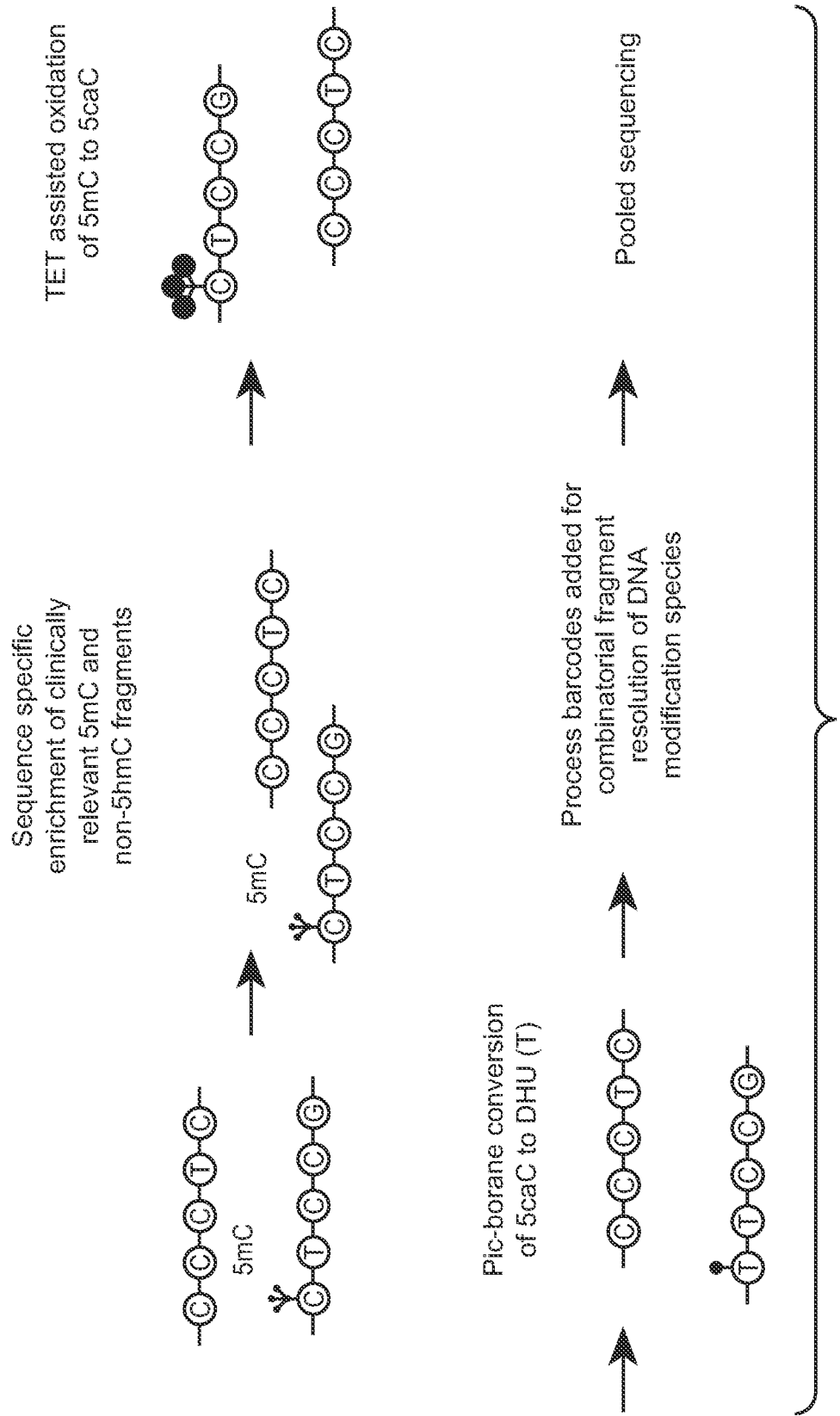
FIG. 18 schematically illustrates an extension of the method of FIG. 17 in which the remaining DNA fragments, including unmodified DNA fragments and 5mC-containing DNA fragments, are analyzed.

The 5mC/5hmC co-occurrence analysis can be extended into a second stage, in order to identify 5mC-containing fragments (fragments that do not contain 5hmC, as 5hmC containing fragments were pulled down in Stage 1). The remaining DNA after Stage 1 includes unmethylated DNA as well as DNA containing 5mC. These fragments are subjected to an oxidation reaction as in Stage 1, using a TET enzyme or the like, thereby converting 5mC residues to 5fC and 5caC residues. An organic borane such as 2-picoline borane converts the 5fC and 5caC residues to DHU, and the method continues with PCR addition of process barcodes, combinatorial fragment resolution of DNA modification species, and pooled sequencing, as in Stage 1. A representative such method is schematically illustrated in FIG. 18.

9. Other Methods

Figure 19:
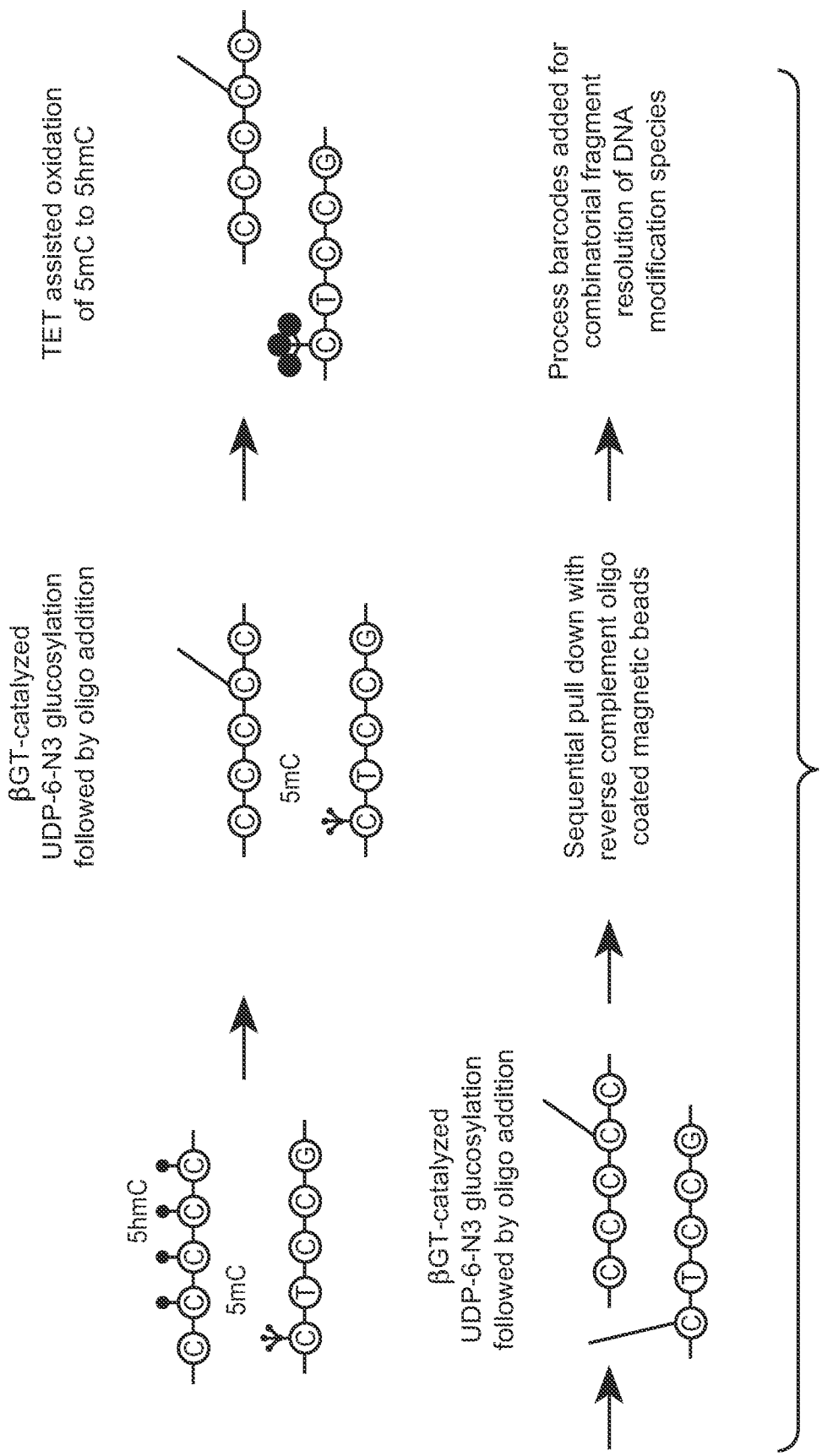
FIG. 19 schematically illustrate a method of the invention in which an oligonucleotide is used as an affinity tag.

In another embodiment, any of the above-described methods can employ a selected oligonucleotide of known sequence as an affinity tag for 5hmC sites, so that hybridization with a support-bound probe having a sequence complementary to that oligonucleotide can be used to pull down oligonucleotide-tagged 5hmC sites. An example of this method is provided in the scheme of FIG. 19.

---

The invention claimed is:

1. A method for detecting the locations of 5mC and 5hmC residues in a cell-free DNA sample comprising fragmented, adapter-ligated template DNA, wherein the method comprises:

in a first fraction of the sample,
- (a) blocking 5hmC residues with a blocking reagent to yield blocked 5hmC residues;
- (b) enzymatically oxidizing 5mC residues to provide oxidized 5mC residues selected from 5caC, 5fC, and combinations thereof;
- (c) converting the oxidized 5mC residues to DHU by treatment with pyridine borane, thereby providing first fraction DNA comprising blocked 5hmC residues and DHU at 5mC locations; and
- (d) amplifying and sequencing the first fraction DNA to provide first fraction sequence reads in which the blocked 5hmC residues read as C and DHU reads as T; and and in a second fraction of the sample,
- (e) oxidizing 5hmC residues with an oxidizing reagent effective to convert 5hmC residues to oxidized 5hmC residues without modifying 5mC residues, wherein the oxidized 5hmC residues are selected from 5caC, 5fC, and combinations thereof; and
- (f) converting the oxidized 5hmC residues to DHU by treatment with pyridine borane, thereby providing second fraction DNA comprising unmodified 5mC residues and DHU in place of the oxidized 5hmC residues;
- (g) amplifying and sequencing the second fraction DNA to provide second fraction sequence reads in which the unmodified 5mC residues read as C and DHU reads as T; and
- (h) comparing the first fraction sequence reads with the second fraction sequence reads to identify 5mC and 5hmC locations in the template DNA.

2. The method of claim 1, wherein the blocking reagent comprises β-glucosyltransferase, such that the blocking group provided in step (a) is glucose.

3. The method of claim 1, wherein step (b) is carried out using a TET enzyme.

4. The method of claim 3, wherein the TET enzyme comprises TET2.

5. The method of claim 1, wherein the oxidizing reagent in step (e) is a chemical oxidizing reagent.

6. The method of claim 5, wherein the chemical oxidizing reagent is a perruthenate salt.

7. The method of claim 6, wherein the perruthenate salt is potassium perruthenate.

8. The method of claim 1, wherein the cell-free DNA comprises double-stranded DNA.

9. The method of claim 1, wherein the cell-free DNA comprises single-stranded DNA.

10. The method of claim 1, wherein the adapter-ligated DNA comprises adapters containing a sample identifier sequence and at least one additional molecular barcode selected from a fragment identifier sequence and a strand identifier sequence.

11. The method of claim 1, further including appending a non-sequence-related molecular barcode to the first fraction DNA, to the second fraction DNA, or to both the first fraction DNA and the second fraction DNA, during amplification.

* * * * *